United States Patent [19]

Pees et al.

[11] Patent Number: 5,593,996
[45] Date of Patent: Jan. 14, 1997

[54] TRIAZOLOPYRIMIDINE DERIVATIVES

[75] Inventors: Klaus-Jurgen Pees, Mainz; Guido Albert, Hackenheim, both of Germany

[73] Assignee: American Cyanamid Company, Madison, N.J.

[21] Appl. No.: 412,401

[22] Filed: Mar. 28, 1995

Related U.S. Application Data

[63] Continuation-in-part of Ser. No. 276,384, Jul. 18, 1994, abandoned, which is a continuation of Ser. No. 998,113, Dec. 29, 1992, abandoned.

[30] Foreign Application Priority Data

Dec. 30, 1991 [EP]  European Pat. Off. ............... 9112422

[51] Int. Cl.$^6$ ................... C07D 487/04; A01N 43/50
[52] U.S. Cl. ................... 514/258; 514/183; 514/212; 514/227.5; 514/234.2; 540/481; 540/600; 544/56; 544/118; 544/263
[58] Field of Search .................. 544/263, 118; 514/234.2, 258

[56] References Cited

U.S. PATENT DOCUMENTS

| | | | |
|---|---|---|---|
| 4,036,840 | 7/1977 | OBrien et al. | 546/263 |
| 4,189,483 | 2/1980 | Snowling | 514/258 |
| 4,199,584 | 4/1980 | Cox et al. | 514/258 |
| 4,567,263 | 1/1986 | Eicken et al. | 544/263 |
| 4,617,303 | 10/1986 | Eicken et al. | 544/263 |
| 5,250,530 | 10/1993 | Giencke et al. | 514/256 |

FOREIGN PATENT DOCUMENTS

| | | | |
|---|---|---|---|
| 0071792 | 2/1983 | European Pat. Off. | 544/263 |
| 550113 | 7/1993 | European Pat. Off. | 544/263 |
| 1148629 | 4/1969 | United Kingdom. | |
| 94-20501 | 9/1996 | WIPO | 514/263 |

OTHER PUBLICATIONS

Tenor et al. Chem Abstr vol. 70 entry 47491w (1968).

*Primary Examiner*—Donald G. Daus
*Attorney, Agent, or Firm*—Joseph M. Mazzarese

[57] ABSTRACT

This invention relates to certain triazolopyrimidine derivatives of formula I

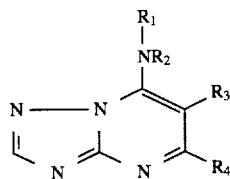

wherein $R_1$ represents an optionally substituted alkyl, alkenyl, alkynyl, alkadienyl, cycloalkyl, bicycloalkyl or heterocyclyl group; $R_2$ represents a hydrogen atom or an alkyl group; or $R_1$ and $R_2$ together with the interjacent nitrogen atom represent an optionally substituted heterocyclic ring; $R_3$ represents an optionally substituted aryl group; and $R_4$ represents a hydrogen or halogen atom or a group —$NR_5R_6$ where $R_5$ represents a hydrogen atom or an amino, alkyl, cycloalkyl or bicycloalkyl group and $R_6$ represents a hydrogen atom or an alkyl group; processes for their preparation; compositions containing such compounds and their use as fungicides.

13 Claims, No Drawings

TRIAZOLOPYRIMIDINE DERIVATIVES

This is a continuation-in-part of application Ser. No. 08/276,384 filed on Jul. 18, 1994, now abandoned, which is continuation of application Ser. No. 07/998,113 filed on Dec. 29, 1992, now abandoned.

This invention relates to certain triazolopyrimidine derivatives, a process for their preparation, compositions containing such compounds and their use as fungicides.

EP-A-0071792 discloses compounds of the general formula

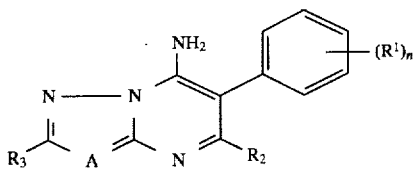

in which $R_1$ represents alkyl, halogen, alkoxy, cyano, cycloalkyl, aryl, aryloxy, arylthio, arylalkyl, arylalkyloxy or arylalkylthio each optionally substituted by halogen or alkoxy, or $(R^1)_n$ represents a benzene, indane or tetrahydronaphthalene ring fused with the phenyl ring, aromatic moieties in the above groups being optionally substituted by alkyl, alkoxy, halogen or cyano; n is 1 or 2; $R_2$ and $R_3$ are each hydrogen, alkyl or aryl, A represents a nitrogen atom or a $CR_4$ group; and $R_4$ is as $R_2$ but can also be halogen, cyano or alkoxycarbonyl or together with $R_3$ can form an alkylene chain containing up to 2 double bonds. The compounds are said to be active against various phytopathogenic fungi, especially those of the phycomycete class. However, evidence of fungicidal activity is only provided for 17 of the 80 disclosed compounds against Plasmopara viticola, a member of the phycomycete class of fungi.

A new class of triazolopyrimidine derivatives has now been discovered which exhibits a different spectrum of fungicidal activity, the new compounds being active against fungi which are members of the oomycota such as Venturia inaequalis, Botrytis cinerea and Alternaria solani, Erysiphe graminis, Leptosphaeria nodorum, Micronectriella nivalis, Monilinia fructigena, Mycopshaerella ligulicola, Mycosphaerella pinodes, Sclerotinia sclerotiorum, Uncinula necator, Cercospora beticola, Cladosporium herbarum, Helminthosporium tritici repentis, Pyricularia oryzae, Corticium rolfsii, Rhizoctonia solani and the like.

According to the invention there is provided a compound of formula I

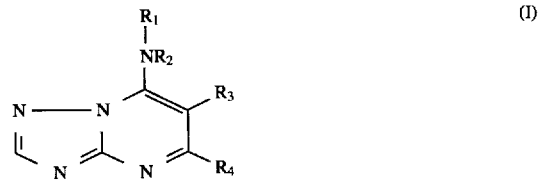

wherein $R_1$ represents an optionally substituted alkyl, alkenyl, alkynyl, alkadienyl, cycloalkyl, bicycloalkyl or heterocyclyl group; $R_2$ represents a hydrogen atom or an alkyl group; or $R_1$ and $R_2$ together with the interjacent nitrogen atom represent an optionally substituted heterocyclic ring; $R_3$ represents an optionally substituted aryl group; and $R_4$ represents a hydrogen or halogen atom or a group—$NR_5R_6$ where $R_5$ represents a hydrogen atom or an amino, alkyl, cycloalkyl or bicycloalkyl group and $R_6$ represents a hydrogen atom or an alkyl group.

When the compounds of this invention contain an alkyl, alkenyl, alkynyl or alkadienyl substituent group, this may be linear or branched and may contain up to 12, preferably up to 6 and especially up to 4, carbon atoms. A cycloalkyl group may contain from 3 to 8, preferably 3 to 6, carbon atoms. A bicycloalkyl group may contain from 4 to 12, preferably 4 to 8, carbon atoms. An aryl group may be any aromatic hydrocarbon group, especially a phenyl or naphthyl group. A heterocyclic ring may be any saturated or unsaturated ring system containing at least one heteroatom, 3- to 12-membered rings being preferred and 5- to 10-membered rings being more preferred. A heterocyclic ring may be a single ring, a bicyclic ring system or a system of annelated or spiro-fused rings. A heterocyclic ring may also contain one or more additional heteroatoms such as oxygen and/or sulfur atoms. Heterocyclic rings such as pyrrolidinyl, piperidyl, dihydropiperidyl, dihydropyridinyl, piperazinyl, morpholinyl, thiazinyl, azepanyl, azocanyl and dioxa-aza-spiro-decyl preferred.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, especially furyl, and cycloalkyl, especially cyclopropyl, groups. Typically, 0–3 substituents may be present. When any of the foregoing substituents represents or contains an alkyl substituent group, this may be linear or branched and may contain up to 12, preferably up to 6, and especially up to 4, carbon atoms. When any of the foregoing substituents represents or contains an aryl or cycloalkyl moiety, the aryl or cycloalkyl moiety may itself be substituted by one or more halogen atoms, nitro, cyano, alkyl, haloalkyl, alkoxy or haloalkoxy groups. In the case of cycloalkyl and heterocyclyl groups, optional substituents also include groups which together with two adjacent carbon atoms of the cycloalkyl or heterocyclyl group form a saturated or unsaturated hydrocarbyl ring. In other words, a saturated or unsaturated hydrocarbyl ring may be optionally fused with the cycloalkyl or heterocyclyl group.

It is preferred that $R_1$ represents a $C_{1-12}$alkyl, $C_{2-6}$alkenyl, $C_{2-6}$alkynyl, $C_{4-12}$alkadienyl, $C_{3-8}$cycloalkyl or $C_{4-8}$bicycloalkyl group or a 3- to 6-membered heterocyclic ring, each group or ring being optionally substituted by one or more substituents selected from halogen atoms, nitro, cyano, hydroxyl, $C_{1-4}$alkyl, $C_{1-4}$haloalkyl, $C_{1-4}$alkoxy, $C_{1-4}$haloalkoxy, amino, $C_{1-4}$alkylamino, di-$C_{1-4}$alkylamino, formyl, $C_{1-4}$alkoxycarbonyl, carboxyl, phenyl, $C_{1-4}$haloalkylphenyl, di-$C_1$-$C_4$alkoxyphenyl, furyl and dihalo-$C_{3-6}$cycloalkyl groups, or in the case where $R_1$ represents a $C_{3-8}$cycloalkyl group or a 3- to 6-membered heterocyclic ring, optionally ortho-fused with a benzene ring.

More preferably, $R_1$ represents a $C_{1-12}$alkyl, $C_{2-6}$alkenyl, alkenyl, $C_{2-4}$alkynyl, $C_{4-8}$alkadienyl, $C_{3-8}$cycloalkyl, $C_{4-8}$bicycloalkyl group or a 3- to 6-membered nitrogen-containing heterocyclic ring, each group or ring being optionally substituted by up to three substituents selected from halogen, especially chlorine, hydroxyl, $C_{1-4}$alkyl, alkyl, especially methyl, $C_{1-4}$haloalkyl, especially trifluoromethyl, $C_{1-4}$alkoxy, especially methoxy, $C_{1-4}$haloalkoxy, especially trifluoromethoxy, phenyl, $C_{1-4}$haloalkylphenyl, di-$C_{1-4}$alkoxyphenyl, furyl and dihalo $C_{3-6}$cycloalkyl groups or, in the case where $R_1$ represents a $C_{3-8}$ cycloalkyl group or a 3- to the 6-membered heterocyclic ring, optionally ortho-fused with a benzene ring.

Preferably, $R_2$ represents a hydrogen atom or a $C_{1-4}$alkyl group.

More preferably, $R_1$ and $R_2$ together with the interjacent nitrogen atom, represent an optionally substituted 3- to 12-membered heterocyclic ring optionally substituted with one or more substituents selected from halogen atoms, nitro, $C_{1-4}$alkyl and $C_{1-4}$haloalkyl groups. Particularly preferred are those formula I compounds wherein $R_1$ and $R_2$ together with the interjacent nitrogen atom represent a 5- to 10-membered heterocyclic ring optionally substituted with one or more substituents selected from halogen atoms, $C_{1-4}$alkyl and $C_{1-4}$haloalkyl groups. The more preferred optionally substituted heterocyclic rings are $C_{1-4}$alkyl-substituted pyrrolidinyl, piperidyl, dihydropiperidyl, dihydropyridinyl, thiazanyl, azepanyl, azocanyl or dioxa-aza-spiro decyl It is also preferred that $R_3$ represents a phenyl or naphthyl group, each group being optionally substituted by one or more substituents selected from halogen atoms, nitro, cyano, hydroxyl, $C_{1-12}$alkyl, $C_{1-12}$haloalkyl, $C_{1-12}$-alkoxy, $C_{1-12}$haloalkoxy, amino, $C_{1-4}$alkylamino, di-$C_{1-4}$-alkylamino, formyl, $C_{1-4}$alkoxycarbonyl, carboxyl, phenyl, phenoxy and benzyloxy groups.

More preferably, $R_3$ represents a phenyl group optionally substituted by up to three substituents selected from halogen atoms, $C_{1-4}$alkyl, $C_{1-4}$haloalkyl, $C_{1-4}$alkoxy, $C_{1-4}$haloalkoxy, phenyl, phenoxy and benzyloxy groups, or a naphthyl group.

Preferably, $R_4$ represents a hydrogen or halogen atom or a group —$NR_5R_6$ where $R_5$ represents a hydrogen atom or an amino, $C_{1-4}$alkyl, especially methyl, $C_{3-6}$cycloalkyl or $C_{4-8}$bicycloalkyl group and $R_6$ represents a hydrogen atom or a $C_{1-4}$alkyl, especially methyl, group.

A particularly preferred sub-group of compounds of formula I is that in which $R_1$ represents a methyl, ethyl, propyl, heptyl, dodecyl, benzyl, dichlorocyclopropylmethyl, furylmethyl, trifluoromethylphenethyl, dimethoxyphenethyl, pentenyl, propynyl, dimethyloctadienyl, cyclopropyl, cyclopentyl, hydroxycyclopentyl, trimethylcyclopentyl, cyclohexyl, trimethylcyclohexyl, cyclooctyl, indanyl, bicycloheptyl, dichloroaziridinyl, pyrrolidinyl, morpholinyl or benzothiazolyl group; $R_2$ represents a hydrogen atom, methyl or ethyl group; or $R_1$ and $R_2$ together with the interjacent nitrogen atom represent a phenylpiperidyl group; $R_3$ represents a phenyl, fluorophenyl, chlorophenyl, bromophenyl, chlorofluorophenyl, methylphenyl, propylphenyl, trifluoromethylphenyl, methoxyphenyl, ethoxyphenyl, dimethoxyphenyl, trimethoxyphenyl, trifluoromethoxyphenyl, biphenylyl, phenoxyphenyl, benzyloxyphenyl or naphthyl group; and $R_4$ represents a hydrogen, fluorine, chlorine, bromine, or iodine atom or an amino, methylamino, dimethylamino, hydrazino, cyclopentylamino or bicycloheptylamino group.

An especially preferred sub-group of compounds of formula I is that in which $R_1$ and $R_2$ together represent an optionally $C_{1-4}$-alkyl-substituted pyrrolidinyl, piperidyl, dihydropiperidyl dihydropyridinyl, thiazanyl, azepanyl, azocanyl or dioxa-aza-spiro decyl group; $R_3$ represents a phenyl, fluorophenyl, chlorophenyl, bromophenyl, chlorofluorophenyl, difluorophenyl, dichlorophenyl, methylphenyl, trifluoromethylphenyl, tert-butylphenyl or chloronitrophenyl group; and $R_4$ represents a hydrogen, fluorine, chlorine or bromine atom.

Especially good results in terms of control of phytopathogenic fungi are obtained by using, for example, the following compounds of formula I: 5-chloro-6-(2,6-dichlorophenyl)-7-(2-methyl-piperidin-1-yl)-[1,2,4]triazolo[1,5-a]pyrimidine; 5-chloro-6-(2,6-dichlorophenyl)-7-(2-methyl-pyrrolidin-1-yl)-[1,2,4]triazolo[1,5-a]pyrimidine; 5-chloro-6-(2,6-difluorophenyl)-7-(2-methyl-pyrrolidin-1-yl)-[1,2,4]triazolo[1,5-a]pyrimidine; 5-chloro-6-(2,6-difluorophenyl)-7-(2-methyl-pyrrolidin-1-yl)-[1,2,4]triazolo[1,5a]pyrimidine; 5-chloro-6-(2,6-difluorophenyl)-7-(4-methyl-pyrrolidin-1-yl)-[1,2,4]triazolo[1,5a]pyrimidine; 5-chloro-6-(2-chlor-6-fluorophenyl)-7-([1,4]thiazinan-4-yl)-[1,2,4]triazolo[1,5a]pyrimidine; 5-chloro-6-(2-chlor-6-fluorophenyl)-7-(1,4-dioxa-8-aza-spiro[4.5]dec-8yl)-[1,2,4]triazolo[1,5a]pyrimidine; 5-chloro-6-(2-chlor-6-fluorophenyl)-7-(3,6-dihydro-2H-pyridin-1-yl)-[1,2,4]triazolo[1,5a]pyrimidine; 5-chloro-6-(2-chloro-6-fluorophenyl)-7-(2-ethyl-piperidin-1-yl)-[1,2,4]triazolo[1,5a]pyrimidine; 5-chloro-6-(2-chloro-6-fluorophenyl)-7-(2-methyl-piperidin-1-yl)-[1,2,4]triazolo[1,5-a]pyrimidine; 5-chloro-6-(2-chloro-6-fluorophenyl)-7-(2-methyl-pyrrolidin-1-yl)-[1,2,4]-triazolo[1,5-a]pyrimidine; 5-chloro-6-(2-chloro-6-fluorophenyl)-7-(4-methyl-piperidin-1-yl)-[1,2,4]triazolo[1,5-a]pyrimidine; 5-chloro-6-(2-chlorophenyl)-7-(2-methyl-piperidin-1-yl)-[1,2,4]triazolo[1,5a]pyrimidine; 5-chloro-6-(2-chloro-phenyl)7-(2-methyl-pyrrolidin-1-yl)-[1,2,4]triazolo [1,5-a]pyrimidine; 5-chloro-6-(2-chlorophenyl)-7-(4-methyl-piperidin-1-yl)-[1,2,4]triazolo[1,5a]pyrimidine; 5-chloro-6-(2-fluoro-phenyl)-7-(2-methyl-piperidin-1-yl)-[1,2,4]triazolo[1,5a]pyrimidine; 5-chloro-6-(2-fluoro-phenyl)-7-(2-methyl-pyrrolidin-1-yl)-[1,2,4]triazolo[1,5a]pyrimidine; 5-chloro-6-(3,4-difluorophenyl)-7-(2-methyl-piperidin-1-yl)-[1,2,4]triazolo[1,5a]pyrimidine; 7-azepan-1-yl-5-chloro-6-(2,6-difluorophenyl)-[1,2,4]triazolo[1,5a]pyrimidine; 7-azepan-1-yl-5-chloro-6-(2-chloro-6-fluorophenyl)-[1,2,4]triazolo[1,5a]pyrimidine; 7-azepan-1-yl-5-chloro-6-(2-chlorophenyl)-[1,2,4]triazolo[1,5a]pyrimidine; 7-azepan-1-yl-5-chloro-6-(2-fluorophenyl)-[1,2,4]triazolo[1,5-a]pyrimidine; 7-azepan-1-yl-5-chloro-6-(3,4-difluorophenyl)-[1,2,4]triazolo[1,5-a]pyrimidine; 7-azocan-1-yl-5-chloro-6-(2-chloro-6-fluorophenyl)-[1,2,4]triazolo[1,5a]pyrimidine.

It will be appreciated that certain of the compounds of the invention, for example those in which $R_3$ is a 2-chloro-6-fluorophenyl group, can exist in different atropoisomeric forms. The present invention is to be understood to include all individual atropoisomeric forms of the compounds of formula I and mixtures thereof in whatever proportion. It will be further appreciated that one atropoisomer may have a greater activity than another atropoisomer of the same compound or than a mixture of the isomers.

The present invention also provides a process for the preparation of a compound of formula I as defined above which comprises (a) reacting a compound of the general formula

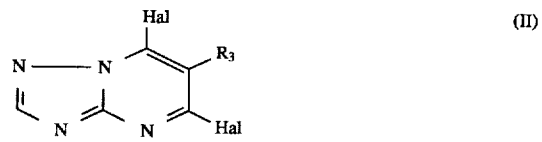

in which $R_3$ is as defined above and Hal represents a chlorine or bromide atom with a compound of the general formula

in which $R_1$ and $R_2$ are as defined above, to produce a compound of formula I in which $R_4$ represents a chlorine or bromine atom;

(b) if desired, reacting the compound of formula I formed in (a) with a fluorinating agent to produce a compound of formula I in which $R_4$ represents a fluorine atom;

(c) if desired, reacting the compound of formula I formed in (a) with a reducing agent to produce a compound of formula I in which $R_4$ represents a hydrogen atom;

(d) if desired, reacting the compound of formula I formed in (a) with a compound of the general formula

$$HNR_5R_6 \qquad (IV)$$

in which $R_5$ and $R_6$ are as defined above, to produce a compound of formula I in which $R_4$ represents a group $-NR_5R_6$; and (e) if desired, reacting a compound of formula I formed in (d) in which $R_5$ and $R_6$ both represent a hydrogen atom with diiodomethane in the presence of a diazotising agent to produce a compound of formula I in which $R_4$ represents an iodine atom.

The process of step (a) is conveniently carried out in the presence of a solvent. Suitable solvents include ethers, such as dioxane, diethyl ether and, especially, tetrahydrofuran, halogenated hydrocarbons, such as dichloromethane, and toluene. The reaction is suitably carried out at a temperature in the range from 0° C. to 70° C., the preferred reaction temperature being from 10° C. to 35° C. It is also preferred that the reaction is carried out in the presence of a base. Suitable bases include tertiary amines, such as triethylamine, and inorganic bases, such as potassium carbonate or sodium carbonate. Alternatively, an excess of the compound of formula III may serve as a base.

The process of step (b) is conveniently carried out in the presence of a solvent. Suitable solvents include sulpholane, dimethylformamide or a mixture of acetonitrile and crown ether. If sulpholane or dimethylformamide is used as solvent, it is advantageous to use toluene as a co-solvent to aid dehydration of the fluorinating agent. The reaction is suitably carried out at a temperature in the range from room temperature (about 15° C.) to the reflux temperature of the reaction mixture, the preferred reaction temperature being from 40° C. to the reflux temperature of the reaction mixture. Suitable fluorinating agents include alkali metal fluorides, especially potassium fluoride, and antimony fluoride.

The reducing agent utilized in step (c) is conveniently a catalytic hydrogenating agent, that is, hydrogen gas used under elevated pressure in the presence of a catalyst. Preferably, the catalyst is palladium on charcoal. It is also preferred that this step is carried out in the presence of a base. Suitable bases include tertiary amines, such as triethylamine, and inorganic bases, such as sodium carbonate or, especially, sodium hydroxide. This step may also be conveniently carried out in the presence of a solvent. Suitable solvents include alcohols, such as methanol. The reaction is suitably carried out at a temperature in the range from 0° C. to 70° C., the preferred reaction temperature being from 10° C. to 35° C.

The process of step (d) is conveniently carried out in the presence of a solvent. Suitable solvents include ethers, such as dioxane, diethyl ether and tetrahydrofuran, halogenated hydrocarbons, such as dichloromethane, and, especially, toluene. The reaction is suitably carried out at a temperature in the range from 20° C. to the reflux temperature of the reaction mixture, the preferred reaction temperature being from 40° C. to the reflux temperature of the reaction mixture.

It is also preferred that the reaction is carried out in the presence of a base. Suitable bases include tertiary amines, such as triethylamine, and inorganic bases, such as potassium carbonate or sodium carbonate. Alternatively, an excess of the compound of formula IV may serve as a base.

When $R_1$ represents the same substituent as $R_5$ and $R_2$ represents the same substituent as $R_6$ in the resultant compound of formula I, the compound of formula III will be the same as the compound of formula IV and steps (a) and (d) may therefore be performed as one step by using double the quantity of amine of formula III/IV.

The diazotising agent used in step (e) may be any alkyl ester of nitrous acid, isopentyl nitrite being especially preferred. If an alkyl ester of nitrous acid is used, this may also serve as a co-solvent with the diiodomethane. The reaction is suitably carried out at a temperature from 60° C. to 120° C., the preferred reaction temperature being from 70° C. to 110° C.

Compounds of formula II may be prepared by reacting a compound of the general formula

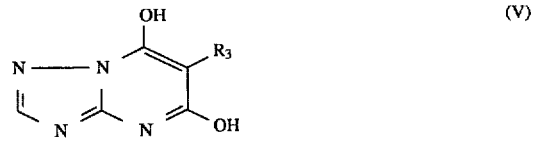

in which $R_3$ is as defined above, with a chlorinating or brominating agent, such as phosphorus oxychloride or phosphorus oxybromide.

Compounds of formula V can be prepared by reacting 3-amino-1,2,4-triazole with an appropriate malonic acid ester under alkaline conditions according to the method of Y. Makisumi, Chem. Pharm. Bull., 9, 801, (1961).

Compounds of formula III and IV are known compounds or can be prepared by processes analogous to known processes.

The inventive compounds of formula I are oils, gums, or predominantly crystalline solid materials. They are superior through their valuable fungicidal properties. For example, they can be used in agriculture or related fields for the control of phytopathogenic fungi such as *Alternaria solani, Botrytis cinerea, Cercospora beticola, Cladosporium herbarum, Corticium rolfsii, Erysiphe graminis, Helminthoporium tritici repentis, Leptosphaeria nodorum, Micronectriella nivalis, Monilinia fructigena, Mycosphaerella ligulicola, Mycosphaerella pinodes, Rhizoctonia solani* and *Sclerotinia sclerotiorum*. The compounds of formula I possess a high fungicidal activity within a wide concentration range and may be used in agriculture without any difficulties.

Accordingly, the invention further provides a fungicidal composition which comprises a carrier and, as active ingredient, a compound of formula I as defined above. A method of making such a composition is also provided which comprises bringing a compound of formula I as defined above into association with at least one carrier. Such a composition may contain a single compound or mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilizers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosene and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% wt/wt of active ingredient and usually contain in addition to solid inert carrier, 3–10% wt/wt of a dispersing agent and, where necessary, 0–10% wt/wt of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5–10% wt/wt of active ingredient. Granules are usually prepared to have a size between 10 and 100 BS mesh (1.676–0.152 mm), and may be manufactured by agglomeration or impregnation techniques. Generally, granules will contain 0.5–75% wt/wt active ingredient and 0–10% wt/wt of additives such as stabilizers, surfactants, slow release modifiers and binding agents. Dry flowable powders consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilizers, penetrants and corrosion inhibitors. Suspension concentrates are usually compounded so as to obtain a stable, non-sedimenting flowable product and usually contain 10–75% wt/wt active ingredient, 0.5–15% wt/wt of dispersing agents, 0.1–10% wt/wt of suspending agents such as protective colloids and thixotropic agents, 0–10% wt/wt of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

In general, the compositions of the invention may be in a concentrated form for the convenience of the end-user who employs diluted compositions. The compositions may be diluted to a concentration of as low as 0.001% of active ingredient (a.i.). The doses usually are in the range of about 0.01 to 10 kg a.i./ha.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include vines, grain crops such as wheat and barley, apples and tomatoes. The duration of protection is normally dependent on the individual compound selected, and also a variety of external factors, such as climate, the impact of which is normally mitigated by the use of a suitable formulation.

The invention is further illustrated by the following examples.

EXAMPLE 1

Preparation of 5-chloro-6-(4-methylphenyl)-7-cyclopentylamino-1,2,4-triazolo[1,5-a]pyrimidine ($R_1$=cyclopentyl; $R_2$=H; $R_3$=4-methylphenyl; $R_4$=Cl)

5,7 Dichloro-6-(4-methylphenyl)-1,2,4-triazolo-[1,5-a]pyrimidine (1.8 g, 6 mmol) was dissolved in tetrahydrofuran. A solution of cyclopentylamine (0.51 g, 6 mmol) and triethylamine (0.61 g, 6 mmol) in tetrahydrofuran (2 ml) was then added with stirring and the stirring continued for a further 3 hours at ambient temperature (20° C.). The reaction mixture was then evaporated in vacuo and the residue extracted with dichloromethane and water (100 ml each). The organic layer was dried over sodium sulphate and the solvent evaporated in vacuo. The residue was crystallized from ethyl acetate to give 1.7 g 5-chloro-6-(4-methylphenyl)-7-cyclopentylamino-1,2,4-triazolo[1,5-a]pyrimidine as yellowish crystals, m.pt. 158° C. Yield: 87% of theoretical $_1$H-NMR: δ=1.3–1.75 (2 m, 8H); 2.43(s,1H); 3.73 (m,1H); 5.97 (d,1H); 7.25 (m,4H); 8.25(s,1H) ppm

EXAMPLE 2

Preparation of 5-bromo-6-phenyl-7-cyclopentylamino-1,2,4-triazolo-[1,5-a]pyrimidine ($R_1$=cyclopentyl; $R_2$=H; $R_3$=phenyl; $R_4$=Br)

5,7-Dibromo-6-phenyl-1,2,4-triazolo[1,5-a]-pyrimidine (2 g, 5.7 mmol) was dissolved in tetrahydrofuran (40 ml). A solution of triethylamine (0.61 g, 6 mmol) and cyclopentylamine (0.51, 6 mmol) in tetrahydrofuran (5 ml) was then added whilst stirring and the stirring continued for a further 2 hours at ambient temperature (20° C.). The reaction mixture was then evaporated in vacuo and the residue extracted with ethyl acetate and water (100 ml each). The organic layer was dried over sodium sulphate and the solvent evaporated in vacuo. Column chromatography of the residue on a silica gel column (3.5×15 cm) using 3:7 ethyl acetate: petroleum ether as eluant gave 0. 6 g 5-bromo-6-phenyl-7-cyclopentylamino-1,2,4-triazolo-[1,5-a]pyrimidine as a yellowish oil.

Yield: 28% of theoretical.

$_1$H-NMR: δ=1.3–1.7 (2 m, 8H); 3.64 (m,1H); 6.05(d,1H); 7.34 (m,2H); 7.50 (m,3H); 8.26 (s,1H) ppm.

EXAMPLE 3

Preparation of 6-(4-methoxyphenyl)-7-cyclopentylamino1,2,4-triazolo[1,5-a]pyrimidine ($R_1$=cyclopentyl; $R_2$=H; $R_3$=4-methoxyphenyl; $R_4$=H)

5-Chloro-6-(4-methoxyphenyl)-7-cyclopentylamino1,2,4-triazolo[1,5-a]pyrimidine (5.1 g, 14.8 mmol), prepared by a method analogous to Example 1, was dissolved in a mixture of methanol (100 ml) and aqueous sodium hydroxide (1N, 15 ml), palladium (0.5 g; on charcoal, 5% E 10N) was added and the reaction mixture stirred for 3 hours under hydrogen (5 bar). The catalyst was removed by filtration and the filtrate evaporated in vacuo. Column chromatography of the residue on a silica gel column (3.5×15 cm) using 4:1 ethyl acetate: petroleum ether as eluant and evaporation of the solvent in vacuo gave 2.6 g 6-(4-methoxyphenyl)-7-cyclopentylamino-1,2,4-triazolo-[1,5-a]pyrimidine as colourless crystals, m.pt. 127° C. Yield: 57% of theoretical $_1$H-NMR: δ=1.35–1.75 (2 m,8H); 3.88 (s,3H); 6.16 (d,1H); 7.00 (dd,2H); 7.34 (m,2H); 8.32 (s,1H); 8.34 (s,1H) ppm

EXAMPLE 4

Preparation of 5-methylamino-6-phenyl-7-cyclopentylamino-1,2,4-triazolo[1,5-a]pyrimidine ($R_1$=cyclopentyl; $R_2$=H; $R_3$=phenyl; $R_4$=NR$_5$R$_6$;R$_5$=CH$_3$; R$_6$=H)

A mixture of 5-chloro-6-phenyl-7-cyclopentylamino-1,2,4-triazolo[1,5-a]pyrimidine (3.1 g, 10 mmol) prepared by a method analogous to Example 2, methylamine (5 ml), triethylamine (5 ml) and toluene (50 ml) was refluxed for 10 hours. After cooling, the reaction mixture was washed with water (50 ml) and the organic layer separated, dried over sodium sulphate and evaporated. Recrystallization of the solid residue from diisopropyl ether gave 2.3 g 5-methylamino-6-phenyl-7-cyclopentylamino-1,2,4-triazolo[1,5-a] pyrimidine as colourless crystals, m.pt. 158°–160° C. Yield: 75% of theoretical $_1$H-NMR: δ=1.25–1.7 (mm, 8H); 2.95 (d,3H); 3.42 (m,1H); 4.48 (m,1H); 5.55 (d,1H); 7.3–7.5 (m,5H); 8.03 (s,1H)

EXAMPLE 5

Preparation of 5-fluoro-6-(4-methoxyphenyl)-7-cyclopentylamino-1,2,4-triazolo[1,5-a]pyrimidine ($R_1$=cyclopentyl; $R_2$=H; $R_3$=4-methoxyphenyl; $R_4$=F)

Potassium fluoride (3.1 g, 0.05 mol) was suspended in a mixture of dry sulpholane (60 ml) and toluene (20 ml) and the mixture was then refluxed for 6 hours over a water separator. 5-Chloro-6-(4 methoxyphenyl)-7-cyclopentylamino-1,2,4-triazolo[1,5-1]pyrimidine (8.5 g, 0.025 mol), obtained by a method analogous to that of Example 1 above, was added at room temperature and an azeotrope of sulpholane and toluene distilled off until the reaction temperature reached 200° C. The reaction mixture was then kept at this temperature for 3 days before cooling to room temperature and then pouring into water (600 ml). The mixture was then filtered and the precipitate washed with water. The precipitate was then dissolved in dichloromethane, extracted twice with water, dried with sodium sulphate and the solvent was distilled off in vacuo. The residue was then washed twice with warm diethyl ether, the ether fraction was decanted off and then dried in vacuo. Flash column chromatography on silica gel using a mixture of petroleum ether and ethyl ethanoate as eluant yielded 4.5 g 5-fluoro-6-(4-methoxyphenyl)-7-cyclopentylamino-1,2,4-triazolo[1,5-1-] pyrimidine as a colourless crystalline solid, m.pt. 124° C. Yield: 55% of theoretical.

EXAMPLE 6

Preparation of 5-iodo-6-(2-chlorophenyl)-7-cyclopentylamino-1,2,4-triazolo[1,5-a]pyrimidine ($R_1$=cyclopentyl; $R_2$=H; $R_3$=2-chlorophenyl; $R_4$=I)

5-Amino-6-(2-chlorophenyl)-7-cyclopentylamino 1,2,4-triazolo[1,5-a-]pyrimidine (3.3 g, 10 mmol), obtained by a method analogous to that of Example 4 above, and diiodomethane (50 ml)were mixed together. Isopentyl nitrite (20 ml) was added under nitrogen and the reaction mixture heated for 3 hours at 90° C. The reaction mixture was then cooled to room temperature and filtered. The solvent was distilled off in vacuo and the residue was purified by flash column chromatography on silica gel using 7:3 petroleum ether:ethyl ethanoate as eluant to yield 1.33 g 5-iodo-6-(2-chlorophenyl)-7-cyclopentylamino1,2,4-triazolo-[1,5-a]pyrimidine as colourless crystals, m.pt. 150° C. Yield: 30.3% of theoretical.

EXAMPLES 7 to 117

By processes similar to those described in Examples 1 to 6 above, further compounds according to the invention were prepared as detailed in Table I below. In this table the compounds are identified by reference to formula I. Melting point, NMR and C,H,N analysis data for the compounds of Examples 7 to 117 are given in Table IA below.

TABLE I

| Ex. No. | R¹ | R² | R³ | R⁴ |
|---|---|---|---|---|
| 7 | cyclopentyl | H | 2-OCH₃ phenyl | Cl |
| 8 | " | " | 3-OCH₃ phenyl | " |
| 9 | " | " | 4-OC₂H₅ phenyl | " |
| 10 | 2-OH cyclopentyl | " | 4-OCH₃ phenyl | " |
| 11 | 2,4,4-(CH₃)₃ cyclopentyl | " | phenyl | " |
| 12 | cyclooctyl | " | 4-OCH₃ phenyl | " |
| 13 | 4-phenylpiperidyl | " | phenyl | " |
| 14 | 2,4-(CH₃)₂ pent-3-yl | " | " | " |
| 15 | cyclopentyl | " | 4-OCH₃ phenyl | cyclo-pentyl amino |
| 16 | " | " | " | —NHCH₃ |
| 17 | —CH(CH₃)₂ | " | 4-OC₂H₅ phenyl | Cl |
| 18 | 2,2,5-(CH₃)₃ cyclohexyl | " | phenyl | " |
| 19 | indan-2-yl | " | phenyl | " |
| 20 | —CH₃ | —CH₃ | 3-Cl phenyl | " |
| 21 | —CH(CH₃)₂ | H | 4-CH₃ phenyl | " |
| 22 | cyclopentyl | " | 4-OCH₃ phenyl | " |
| 23 | cyclohexyl | " | phenyl | " |
| 24 | C₁₂H₂₅ | " | " | " |
| 25 | cyclopentyl | " | phenyl | " |
| 26 | cyclopropyl | " | " | " |
| 27 | cyclopentyl | " | 3-CF₃ phenyl | " |
| 28 | " | " | 4-ⁱC₃H₇ phenyl | " |
| 29 | " | " | 4-OCF₃ phenyl | " |
| 30 | " | " | naphth-2-yl | " |
| 31 | " | " | 3,4-(OCH₃)₂ phenyl | " |
| 32 | cyclopentyl | H | 2-Cl phenyl | Cl |
| 33 | " | " | 4-F phenyl | " |
| 34 | " | " | 4-biphenylyl | " |
| 35 | —CH₂C H | " | phenyl | " |
| 36 | benzyl | " | " | " |
| 37 | cyclopentyl | " | 2-Br phenyl | " |
| 38 | —CH(CH₃)₂ | " | " | " |
| 39 | bicyclo[2.2.1]hept-2-yl | " | " | " |
| 40 | cyclopentyl | " | 2-F phenyl | " |
| 41 | —CH(CH₃)₂ | " | " | " |
| 42 | " | " | naphth-2-yl | " |
| 43 | " | " | 2-Cl phenyl | " |
| 44 | " | " | 4-F phenyl | " |
| 45 | —CH₂CH=C(CH₃)₂ | " | phenyl | " |
| 46 | —CH₃ | —CH₃ | 4-OCH₃ phenyl | " |
| 47 | —CH₂CH=C(CH₃)CH₂CH₂CH=C(CH₃)₂ | —H | 4-CH₃ phenyl | " |
| 48 | " | " | 4-OCH₃ phenyl | " |
| 49 | —CH₃ | —CH₃ | " | —N(CH₃)₂ |
| 50 | fur-2-ylmethyl | —H | phenyl | —Cl |
| 51 | benzothiazol-2-yl | " | " | " |
| 52 | morpholin-4-yl | " | " | " |
| 53 | 2-OH cyclopentyl | " | " | " |
| 54 | cyclopentyl | " | 4-OC₆H₅ phenyl | " |
| 55 | —CH(CH₃)₂ | " | 3-CF₃ phenyl | " |
| 56 | " | " | 4-ⁱC₃H₇ phenyl | " |
| 57 | " | " | 4-CF₃O phenyl | " |
| 58 | " | " | 4-OC₆H₅ phenyl | " |
| 59 | " | " | 4-biphenylyl | " |
| 60 | " | " | 3,4-(OCH₃)₂ phenyl | " |
| 61 | cyclopentyl | " | 4-OCH₂C₆H₅ phenyl | " |
| 62 | —CH(CH₃)₂ | —H | 4-OCH₂C₆H₅ phenyl | —Cl |
| 63 | bicyclo[2.2.1]hept-2-yl | " | 4-OCH₃ phenyl | " |
| 64 | " | " | 2-Cl phenyl | " |
| 65 | cyclopentyl | " | 4-Br phenyl | " |
| 66 | —CH(CH₃)₂ | " | " | " |
| 67 | bicyclo[2.2.1]hept-2-yl | " | " | " |
| 68 | " | " | 3-Br phenyl | " |
| 69 | cyclopentyl | " | " | " |
| 70 | bicyclo[2.2.1]hept-2-yl | " | 2-F phenyl | " |
| 71 | cyclopentyl | " | 3-F phenyl | " |
| 72 | —CH(CH₃)₂ | " | " | " |
| 73 | bicyclo[2.2.1]hept-2-yl | " | " | " |
| 74 | cyclopentyl | " | 2-OCH₂C₆H₅ phenyl | " |
| 75 | —CH(CH₃)₂ | " | " | " |

TABLE I-continued

| Ex. No. | R¹ | R² | R³ | R⁴ |
|---|---|---|---|---|
| 76 | bicyclo[2.2.1]hept-2-yl | " | " | " |
| 77 | cyclopentyl | " | 2,3-(OCH$_3$)$_2$ phenyl | " |
| 78 | —CH(CH$_3$)$_2$ | " | " | " |
| 79 | bicyclo[2.2.1]hept-2-yl | " | " | " |
| 80 | —CH$_2$CH$_2$-(3-CF$_3$ phenyl) | " | 4-OCH$_3$ phenyl | " |
| 81 | " | " | 2-Cl phenyl | " |
| 82 | 2,2-dichloroaziridin-1-yl | " | 4-OCH$_3$ phenyl | " |
| 83 | " | " | 2-Cl phenyl | " |
| 84 | pyrrolidin-1-yl | " | " | " |
| 85 | bicyclo[2.2.1]hept-2-yl | " | 4-OCH$_3$ phenyl | —NH-bicyclo-[2.2.1]-hept-2-yl |
| 86 | " | " | 2-Cl phenyl | —NH-bicyclo-[2.2.1]-hept-2-yl |
| 87 | " | " | 4-OCH$_3$ phenyl | H |
| 88 | bicyclo[2.2.1]hept-2-yl | —H | 2-Cl phenyl | H |
| 89 | cyclopentyl | " | " | —NH—NH$_2$ |
| 90 | cyclopentyl | " | 4-OCH$_3$ phenyl | — |
| 91 | bicyclo[2.2.1]hept-2-yl | " | 2-Cl phenyl | " |
| 92 | 2,2-dichlorocycloprop-1-yl | " | 3,4,5-(OCH$_3$)$_3$ phenyl | —Cl |
| 93 | cyclopentyl | " | 2-F phenyl | —NH—NH$_2$ |
| 94 | bicyclo[2.2.1]hept-2-yl | " | phenyl | —Br |
| 95 | —CH(CH$_3$)$_2$ | " | " | " |
| 96 | 2,2-dichlorocycloprop-1-yl | " | " | " |
| 97 | —CH$_3$ | " | 2-Cl phenyl | —Cl |
| 98 | " | —CH$_3$ | " | " |
| 99 | —C$_2$H$_5$ | —H | " | " |
| 100 | —CH$_3$ | " | 2-F phenyl | " |
| 101 | " | —CH$_3$ | " | " |
| 102 | —C$_2$H$_5$ | —H | " | " |
| 103 | cyclopentyl | " | 4-OCH$_3$ phenyl | —NH$_2$ |
| 104 | " | " | 2-Cl phenyl | " |
| 105 | " | " | 2-Cl,6-F phenyl | —Cl |
| 106 | —CH(CH$_3$)$_2$ | " | " | " |
| 107 | bicyclo[2.2.1]hept-2-yl | " | 2-Cl,6-F phenyl | " |
| 108 | —CH$_2$CH$_2$-(3,4-(OCH$_3$)$_2$phenyl) | " | " | " |
| 109 | —CH$_3$ | —CH$_3$ | " | " |
| 110 | bicyclo[2.2.1]hept-2-yl | —H | 2-Cl phenyl | —NH$_2$ |
| 111 | —C$_2$H$_5$ | —C$_2$H$_5$ | 2-Cl,6-F phenyl | —Cl |
| 112 | " | " | 2-F phenyl | " |
| 113 | " | " | 2-Br phenyl | " |
| 114 | " | " | 2-Cl phenyl | " |
| 115 | " | " | 4-OCH$_3$ phenyl | " |
| 116 | cyclopentyl | —H | " | I |
| 117 | bicyclo[2.2.1]hept-2-yl | " | 2-Cl phenyl | " |

TABLE IA

| Ex. No. | ¹H-NMR(ppm) | M. pt. (°C.) | Elemental Analysis ||||| 
|---|---|---|---|---|---|---|---|
| | | | C || H || N |
| | | | Calc. | Found | Calc. | Found | Calc. | Found |
| 7 | 1.3–1.7(m, 8H), 3.7 (m, 1H), 3.75(s, 3H), 6.1(d, 1H), 7.0 (m, 2H), 7.25(m, 1H), 7.48(dt, 1H), 8.25 (s, 1H) | 121 | | | | | | |
| 8 | 1.35–1.78(m, 8H), 3.75(m, 1H), 3.85 (s, 3H), 6.05(d, 1H), 6.95(m, 3H), 7.88 (dt, 1H), 8.27(s, 1H) | 110 | | | | | | |
| 9 | 1.3–1.8(2m, 8H), 1.45(t, 3H), 3.78 (m, 1H), 4.08(q, 2H), | 118 | | | | | | |

TABLE IA-continued

| Ex. No. | $^1$H-NMR(ppm) | M. pt. (°C.) | Elemental Analysis | | | | | |
|---|---|---|---|---|---|---|---|---|
| | | | C | | H | | N | |
| | | | Calc. | Found | Calc. | Found | Calc. | Found |
| | 6.05(d, 1H), 7.00 (m, 2H), 7.25(m, 2H), 8.25(s, 1H) | | | | | | | |
| 10 | 1.3–2.03(3m, 6H), 3.25(m, 1H), 3.86 (s, 3H), 5.75(d, 1H), 7.02(m, 2H), 7.27 (dd, 1H), 7.44(dd, 1H), 8.20(s, 1H) | 148 | | | | | | |
| 11 | 0.5–1.8(mm, 13H), 6.06(d, 1H), 7.83 (m, 2H), 7.45(m, 3H), 8.28(s, 1H) | 124–130 | | | | | | |
| 12 | 1.1–1.75(m, 14H), 3.55(m, 1H), 3.9 (s, 3H), 6.05(d, 1H), 7.05(dd, 2H), 7.25 (dd, 2H) | 118 | | | | | | |
| 13 | 1.7–1.9(m, 4H), 2.6 (m, 1H), 2.75(m, 2H), 4.84(m, 2H), 7.1–7.5 (mm, 10H), 8.4(s, 1H) | 168 | | | | | | |
| 14 | 0.5–2.7(mm, 15H), 6.45(m, 1H), 7.2–7.6 (mm, 5H), 8.32(s, 1H) | oil | | | | | | |
| 15 | 1.07–2.05(mm, 16H), 3.37(m, 1H), 3.86 (s, 3H), 4.30(d, 1H), 4.45(m, 1H), 4.97 (d, 1H), 7.0(dd, 2H), 7.28(dd, 2H), 8.0 (s, 1H) | oil | | | | | | |
| 16 | 1.3–1.9(mm, 8H), 2.95(d, 3H), 3.87 (s, 3H), 4.40(d, 1H), 5.50(d, 1H), 7.00 m, 2H), 7.24(m, 2H), 8.03(s, 1H) | 180 | | | | | | |
| 17 | 1.03(2s, 6H), 1.46 (t, 3H), 3.67(m, 1H), 4.06(q, 2H), 5.85 (d, 1H), 7.0(d, 2H), 7.23(d, 2H), 8.26 (s, 1H) | 122 | | | | | | |
| 18 | 0.5–1.7(mm, 17H), 3.25(m, 1H), 5.95 (d, 1H), 7.34(m, 2H), 7.47(m, 3H), 8.28 (s, 1H) | 130 | | | | | | |
| 19 | 1.2–1.9(m, 1H), 2.1–2.25(m, 1H), 2.55–2.7(m, 1H), 2.86–2.96 (m, 1H), 5.05(s, 1H), 6.29(d, 1H), 7.12–7.57 (2m, 4H) | oil | | | | | | |
| 20 | | 177–179 | 50.66 | 50.60 | 3.59 | 3.83 | 22.72 | 22.66 |
| 21 | | 113 | 59.69 | 59.59 | 5.34 | 5.33 | 23.20 | 23.33 |
| 22 | 1.3–1.8(2m, 8H), 3.8(m, 1H), 3.90 (s, 3H), 6.03(d, 1H), 6.98(dd, 2H), 7.28 (dd, 2H), 8.27(s, 1H) | 140 | 59.38 | 59.42 | 5.27 | 5.39 | 20.37 | 20.39 |
| 23 | | 130–132 | 62.28 | 62.26 | 5.58 | 5.48 | 21.36 | 21.31 |
| 24 | | 92–94 | 66.76 | 66.74 | 7.79 | 7.78 | 16.91 | 16.79 |
| 25 | 1.3–1.8(2m, 8H), 3.63(m, 1H), 6.08 (d, 1H), 7.35(m, 2H), 7.56(m, 3H), 8.30 (s, 1H) | 125 | 61.23 | 61.15 | 5.13 | 5.16 | 22.32 | 22.33 |
| 26 | | 175 | 58.84 | 58.69 | 4.23 | 4.22 | 24.51 | 24.47 |
| 27 | 1.05–1.86(m, 8H), 2.6(s, 1H), 3.4–3.7 (2m, 2H), 7.60–8.0 | 165 | | | | | | |

TABLE IA-continued

| Ex. No. | ¹H-NMR(ppm) | M. pt. (°C.) | Elemental Analysis | | | | | |
|---|---|---|---|---|---|---|---|---|
| | | | C Calc. | Found | H Calc. | Found | N Calc. | Found |
| | (m, 4H), 8.6(s, 1H) | | | | | | | |
| 28 | 1.05–1.7(mm, 14H), 2.6(s, 2H), 3.05 (m, 1H), 3.46(m, 1H), 7.38–7.44(2m, 4H), 8.68(s, 1H) | 112 | | | | | | |
| 29 | 1.05–1.7(mm, 8H), 2.6(s, 1H), 3.6 (m, 1H), 7.60(dd, 2H), 7.68(dd, 2H), 8.62 s, 1H) | oil | | | | | | |
| 30 | 1.0–1.7(mm, 8H), 2.6(m, 1H), 3.46 (s, 1H), 7.68(m, 3H), 8.1(m, 4H), 8.70 (s, 1H) | 107 | | | | | | |
| 31 | 1.1–1.8(mm, 8H), 3.48(s, 1H), 3.84 (d, 3H), 3.94(d, 3H), 6.9–7.35(m, 3H), 8.63(s, 1H) | oil | | | | | | |
| 32 | 1.34–1.8(m, 8H), 3.55(m, 1H), 6.22 (d, 1H), 7.48–7.55 (m, 4H), 8.32(s, 1H) | 145 | | | | | | |
| 33 | 1.23–1.75(m, 8H), 3.46(s, 1H), 3.72 (m, 1H), 7.45(m, 2H), 7.65(m, 2H), 8.65 | oil | | | | | | |
| 34 | 1.05–1.8(m, 8H), 3.48(s, 1H), 3.74 (m, 1H), 7.48–8.0 (m, 9H), 8.68(s, 1H) | 65 | | | | | | |
| 35 | | 126 | 59.26 | 59.48 | 3.55 | 3.78 | 24.68 | 24.68 |
| 36 | | 105 | 64.37 | 65.69 | 4.20 | 4.36 | 20.85 | 19.50 |
| 37 | | 160 | | | | | | |
| 38 | | 60 | | | | | | |
| 39 | | 140 | | | | | | |
| 40 | | 97 | | | | | | |
| 41 | | 142 | | | | | | |
| 42 | | 150 | | | | | | |
| 43 | | 128 | | | | | | |
| 44 | | 99 | | | | | | |
| 45 | | 95 | | | | | | |
| 46 | | 134 | 56.68 | 56.62 | 5.07 | 5.08 | 22.04 | 22.03 |
| 47 | (CDCl₃): 1.4(s, 3H); 1.55(s, 3H); 1.7(s, 3H); 1.9(m, 2H); 2.4(s, 3H); 3.5(m, 2H); 5.0(m, 1H); 5.1(m, 1H); 6.0(m, 1H); 7.25(m, 4H); 8.3(s, 1H) | | | | | | | |
| 48 | (CDCl₃): 1.4(s, 3H); 1.5(s, 3H); 1.6(s, 3H); 1.9(m, 2H); 3.5(m, 2H); 3.8(s, 3H); 5.0(m, 1H); 5.1(m, 1H); 5.9(t, 1H); 6.9(d, 2H); 7.2(d, 2H); 8.2(s, 1H) | | | | | | | |
| 49 | | 194 | | | | | | |
| 50 | | 100 | | | | | | |
| 51 | | 198 | | | | | | |
| 52 | (CDCl₃): 2.3(m, 2H); 2.6(m, 4H); 3.5(m, 2H); 7.2(s, 1H); 7.25(m, 2H); 7.4(m, 3H); 8.4(s, 1H) | | | | | | | |
| 53 | | 162 (decomp) | | | | | | |
| 54 | (dmso-d₆): 1.2–1.4(m, 2H); 1.6–1.8(m, 6H); 3.7(m, 1H); 7.1–7.3 | | | | | | | |

TABLE IA-continued

| Ex. No. | ¹H-NMR(ppm) | M. pt. (°C.) | Elemental Analysis | | | | | |
|---|---|---|---|---|---|---|---|---|
| | | | C Calc. | Found | H Calc. | Found | N Calc. | Found |
| | (m, 5H); 7.5–7.6 (m, 4H); 7.7(d, 1H); 8.6(s, 1H) | | | | | | | |
| 55 | | 138 | | | | | | |
| 56 | | 100 | | | | | | |
| 57 | | 108 | | | | | | |
| 58 | | 145 | | | | | | |
| 59 | | 65–70 | | | | | | |
| 60 | | 150 | | | | | | |
| 61 | | 138 | | | | | | |
| 62 | (dmso-d₆): 1.1(d, 6H); 3.6(m, 1H); 5.3(s, 2H); 7.2(d, 1H); 7.4–7.6(m, 7H); 8.6(s, 1H) | | | | | | | |
| 63 | (acetone-d₆): 0.5(m, 1H); 0.9 (m, 1H); 1.1(d, 1H); 1.2–1.6(m, 6H); 1.80(m, 1H); 2.2(m, 2H); 3.3(m, 1H);3.9(s, 3H); 6.3(d, 1H); 7.1(m, 2H); 7.4–7.5(m, 2H); 8.4(s, 1H) | | | | | | | |
| 64 | (acetone-d₆): ppm: 0.2–0.4(m, 1H); 0.9(m, 1H); 1.1(m, 1H); 1.2–1.6(m, 5H); 2.20 (m, 2H); 3.2(m, 1H); 6.6(t, 1H); 7.5–7.8 (m, 4H); 8.4(s, 1H) | | | | | | | |
| 65 | | 167 | | | | | | |
| 66 | | 80 | | | | | | |
| 67 | | 180 | | | | | | |
| 68 | | 140 | | | | | | |
| 69 | | 150 | | | | | | |
| 70 | | 174 | | | | | | |
| 71 | | 130 | | | | | | |
| 72 | | 130 | | | | | | |
| 73 | | 170 | | | | | | |
| 74 | (dmso-d₆): 1.3–1.5(m, 4H); 1.5–1.7(m, 4H); 3.7 (m, 1H); 5.1(s, 2H); 6.1(d, 1H); 7.05 (m, 2H); 7.3(m, 6H); 7.4(t, 1H); 8.3(s, 1H) | | | | | | | |
| 75 | (CDCl₃): 1.1(m, 6H); 3.6(m, 1H); 5.1(s, 1H); 5.95(d, 1H); 7.3–7.3(m, 6H); 7.4 (t, 1H); 8.3(s, 1H) | | | | | | | |
| 76 | (CDCl₃): 0.1(m, 1H); 0.7 (m, 1H); 0.8–1.3(m, 7H); 2.0 (m, 1H); 3.0(m, 1H); 4.9(s, 1H); 5.9(m, 1H); 6.8–6.9(m, 2H); 7.0–7.15(m, 6H); 7.25(m, 1H); 8.05(s, 1H) | | | | | | | |
| 77 | | 162 | | | | | | |
| 78 | | 141 | | | | | | |
| 79 | | 73 (amorph.) | | | | | | |
| 80 | | 140 | | | | | | |
| 82 | (CDCl₃): 1.2(t, 1H); 1.6 (t, 1H); 1.8(m, 1H); 3.1(m, 1H); 3.8(m, 1H); 3.9(s, 3H); 6.25(t, 1H); 7.0(d, 2H); 7.3(d, 2H); | 112 | | | | | | |
| 83 | | 68–78 (amorph) | | | | | | |
| 84 | | 240 | | | | | | |

TABLE IA-continued

| Ex. No. | ¹H-NMR(ppm) | M. pt. (°C.) | Elemental Analysis | | | | | |
|---|---|---|---|---|---|---|---|---|
| | | | C Calc. | Found | H Calc. | Found | N Calc. | Found |
| 85 | | 258 | | | | | | |
| 86 | | 170 | | | | | | |
| 87 | (CDCl₃):<br>0.3(m, 1H); 0.9(m, 1H);<br>1.1(d, 1H); 1.2–1.6<br>(m, 5H); 1.7(m, 1H);<br>2.2(m, 1H); 3.4(m, 1H);<br>3.9(s, 3H); 7.0<br>(d, 1H); 7.2(d, 2H);<br>7.5(d, 2H); 8.3<br>(s, 1H); 8.6(s, 1H) | | | | | | | |
| 88 | (dmso-d₆):<br>0.0(m, 1H); 0.7(m, 1H);<br>0.8–1.7(m, 7H);<br>3.1(m, 1H); 6.9(d, 1H);<br>7.4(m, 2H); 7.6(m, 2H);<br>8.2(s, 1H); 8.5(s, 1H) | 122 | | | | | | |
| 89 | (dmso-d₆):<br>1.2–1.4(m, 2H);<br>1.4–1.7(m, 6H);<br>3.4(m, 1H); 4.4(m, 2H);<br>5.8(m, 1H); 6.5(d, 1H);<br>6.9(m, 1H); 7.6(m, 3H);<br>7.8(d, 1H); 8.3(s, 1H) | | | | | | | |
| 90 | | 121 | | | | | | |
| 91 | (dmso-d₆):<br>0–0.2(m, 1H); 0.8(m, 1H);<br>1.0–1.6(m, 6H);<br>2.0(m, 1H); 2.2(m, 1H);<br>2.7(m, 1H); 6.1(d, 1H);<br>7.5(m, 3H); 7.6((d, 1H);<br>8.2(s, 1H) | | | | | | | |
| 92 | | 205 | | | | | | |
| 93 | (dmso-d₆):<br>1.1–1.3(m, 2H);<br>1.4–1.7(m, 6H);<br>3.4(m, 1H); 4.0–4.6<br>(broad, 2H); 6.4<br>(d, 1H); 7.0(broad,<br>1H); 7.2(m, 1H);<br>7.3–7.5(m, 2H);<br>7.6(m, 1H); 8.2(s, 1H) | | | | | | | |
| 94 | (dmso-d₆):<br>0.1(m, 1H); 0.7<br>(m, 1H); 1(m, 1H);<br>1.1–1.6(m, 5H);<br>2.0(m, 1H); 2.1<br>(m, 1H); 3.0(m, 1H);<br>6.9(d, 1H); 7.4–<br>7.6(m, 5H); 8.6<br>(s, 1H) | | | | | | | |
| 95 | | 148 | | | | | | |
| 96 | | 116 | | | | | | |
| 97 | | 112 | | | | | | |
| 98 | | 150 | | | | | | |
| 99 | | 154 | | | | | | |
| 100 | | 210 | | | | | | |
| 101 | | 163 | | | | | | |
| 102 | | 160 | | | | | | |
| 103 | | 213 | | | | | | |
| 104 | | 230 | | | | | | |
| 105 | | 102 | | | | | | |
| 106 | | 140 | | | | | | |
| 107 | | 185 | | | | | | |
| 108 | | 143 | | | | | | |
| 109 | | 138 | | | | | | |
| 110 | | 275 | | | | | | |
| 111 | | 163 | | | | | | |
| 112 | | 150 | | | | | | |
| 113 | (dmso-d₆):<br>1.0(t, 6H); 3.2(m, 2H);<br>3.5(m, 2H); 7.6(m, 2H);<br>7.9(d, 1H); 8.6(s, 1H) | | | | | | | |

TABLE IA-continued

| Ex. No. | ¹H-NMR(ppm) | M. pt. (°C.) | Elemental Analysis C Calc. | C Found | H Calc. | H Found | N Calc. | N Found |
|---|---|---|---|---|---|---|---|---|
| 114 | (dmso-d₆): 1.0(t, 6H); 3.2(q, 4H); 7.3(m, 2H); 7.5(m, 2H); 8.6(s, 1H) | | | | | | | |
| 115 | (dmso-d₆): 1.0(t, 6H); 3.2(q, 4H); 3.8(s, 1H); 7.1(d, 2H); 7.4(d, 2H); 8.6(s, 1H) | | | | | | | |
| 116 | | 200 | | | | | | |
| 117 | | 84 (amorph.) | | | | | | |

EXAMPLE 118

Preparation of 7-azepan-1-yl-5-chloro-6-(2-chloro-6-fluoro-phenyl)-1,2,4-triazolo[1,5-a]pyrimidine R₁R₂azepan-1-yl, R₃=2-chloro-6-fluoro-phenyl, R₄=chloro)

5,7-dichloro-6-(2-chloro-6-fluoro-phenyl)-1,2,4-triazolo[1,5-a]pyrimidine (16 g, 0.05 mol) is suspended in dichloromethane (100 ml). Azepane (4.9 g, 0.05 mol) is added under stirring, followed by triethylamine (5.5 g, 0.055 mol). The reaction temperature (30°–35° C.) is maintained with the aid of an ice bath. Then the reaction mixture is stirred for 3 h at ambient temperature, subsequently washed two times with 1N hydrochloric acid and once with water. The organic layer is separated, dried with anhydrous sodium sulphate and the solvent is evaporated under reduced pressure. Treatment of the resulting light brown oil with t-butyl methyl ether (50 ml) yields beige crystals (16.1 g, 85% of th.) having a melting point of 152°–154° C.

EXAMPLES 119–218

The following examples (structures, Table IIA; physical data, Table IIB) are synthesized analogously to Example 118.

TABLE IIA

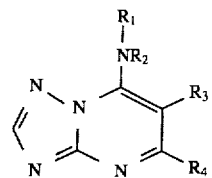
(I)

| Ex. No. | R₁R₂ | R₃ | R₄ |
|---|---|---|---|
| 119 | 4-methylpiperid-1-yl | 2,6-difluorophenyl | Cl |
| 120 | 3-methylpiperid-1-yl | 2,6-difluorophenyl | Cl |
| 121 | 2-methylpiperid-1-yl | 2,6-difluorophenyl | Cl |
| 122 | piperid-1-yl | 2-bromophenyl | Cl |
| 123 | piperid-1-yl | 3-methylphenyl | Cl |
| 124 | piperid-1-yl | 3-fluorophenyl | Cl |
| 125 | piperid-1-yl | 2,6-difluorophenyl | Cl |
| 126 | piperid-1-yl | 2-fluorophenyl | Cl |
| 127 | piperid-1-yl | 2-chloro-5-nitrophenyl | Cl |
| 128 | piperid-1-yl | 2,6-dichlorophenyl | Cl |
| 129 | piperid-1-yl | 2-chloro-6-fluorophenyl | Cl |
| 130 | pyrrolidin-1-yl | 2-chloro-6-fluorophenyl | Cl |
| 131 | morpholin-4-yl | 2-chloro-6-fluorophenyl | Cl |
| 132 | pyrrolidin-1-yl | 2-chlorophenyl | Cl |
| 133 | piperid-1-yl | 2-chlorophenyl | Cl |
| 134 | azepan-1-yl | 2-chlorophenyl | Cl |
| 135 | 3-methylpiperid-1-yl | 2-chlorophenyl | Cl |
| 136 | 4-methylpiperid-1-yl | 2-chlorophenyl | Cl |
| 137 | 2-methylpiperid-1-yl | 2-chlorophenyl | Cl |
| 138 | 3-methylpiperid-1-yl | 2-chloro-6-fluorophenyl | Cl |
| 139 | 4-methylpiperid-1-yl | 2-chloro-6-fluorophenyl | Cl |
| 140 | 2-methylpiperid-1-yl | 2-chloro-6-fluorophenyl | Cl |
| 141 | 3,5-dimethylpiperid-1-yl | 2-chloro-6-fluorophenyl | Cl |
| 142 | 3,5-dimethylpiperid-1-yl | 2-chlorophenyl | Cl |
| 143 | azepan-1-yl | 2-bromophenyl | Cl |
| 144 | azepan-1-yl | 2-chloro-5-nitrophenyl | Cl |
| 145 | azepan-1-yl | 2,6-dichlorophenyl | Cl |
| 146 | azepan-1-yl | 3-chlorophenyl | Cl |
| 147 | azepan-1-yl | phenyl | Cl |
| 148 | azepan-1-yl | 3-trifluoromethylphenyl | Cl |
| 149 | azepan-1-yl | 4-tert-butylphenyl | Cl |
| 150 | azepan-1-yl | 2-fluorophenyl | Cl |
| 151 | azepan-1-yl | 2,6-difluorophenyl | Cl |
| 152 | azepan-1-yl | 3-fluorophenyl | Cl |
| 153 | azepan-1-yl | 3-methylphenyl | Cl |
| 154 | 3,4-dihydro-2H-pyridin-1-yl | 2-chloro-6-fluorophenyl | Cl |
| 155 | 3,3,5-trimethylazepan-1-yl | 2-chloro-6-fluorophenyl | Cl |
| 156 | azocan-1-yl | 2-chloro-6-fluorophenyl | Cl |
| 157 | decahydroquinolin-1-yl | 2-chloro-6-fluorophenyl | Cl |
| 158 | piperazin-1-yl | 2-chloro-6-fluorophenyl | Cl |
| 159 | 3,5-methylpiperazin-1-yl | 2-chloro-6-fluorophenyl | Cl |
| 160 | 3,5-dimethylpiperazin-1-yl | 2-chloro-6-fluorophenyl | Cl |
| 161 | 4-ethylpiperazin-1-yl | 2-chloro-6-fluorophenyl | Cl |
| 162 | 4-methylpiperid-1-yl | 2,6-difluorophenyl | Br |
| 163 | azepan-1-yl | 2,6-difluorophenyl | Br |
| 164 | 4-methylpiperid-1-yl | 2-chloro-6-fluorophenyl | Br |
| 165 | azepan-1-yl | 2-chloro-6-fluorophenyl | Br |
| 166 | 2-hydroxyiminoazepan-1-yl | 2-chloro-6-fluorophenyl | Cl |
| 167 | 3,3-dimethylpiperid-1-yl | 2-chloro-6-fluorophenyl | Cl |
| 168 | triazol-1-yl | 2-chloro-6-fluorophenyl | Cl |

TABLE IIA-continued $$\text{(I)}$$

Structure: pyrazolo-pyrimidine with NR$_2$-R$_1$ at one position, R$_3$ and R$_4$ substituents.

| Ex. No. | R$_1$R$_2$ | R$_3$ | R$_4$ |
|---|---|---|---|
| 169 | 4-hydroxypiperid-1-yl | 2-chloro-6-fluorophenyl | Cl |
| 170 | 4-formylaminopiperid-1-yl | 2-chloro-6-fluorophenyl | Cl |
| 171 | 1,4-dioxa-8-aza-spiro[4.5]dec-8-yl | 2-chloro-6-fluorophenyl | Cl |
| 172 | 2-ethylpiperid-1-yl | 2-chloro-6-fluorophenyl | Cl |
| 173 | 4-benzylpiperid-1-yl | 2-chloro-6-fluorophenyl | Cl |
| 174 | 4-formylpiperazin-1-yl | 2-chloro-6-fluorophenyl | Cl |
| 175 | [1,4]thiazinan-4-yl | 2-chloro-6-fluorophenyl | Cl |
| 176 | 4-cyclopentylpiperazin-1-yl | 2-chloro-6-fluorophenyl | Cl |
| 177 | 2,4-dimethylpiperid-1-yl | 2-chloro-6-fluorophenyl | Cl |
| 178 | 2-carbomethoxypyrrolidin-1-yl | 2-chloro-6-fluorophenyl | Cl |
| 179 | 3-methylpiperid-1-yl | 4-tert-butylphenyl | " |
| 180 | 3-methylpiperid-1-yl | 3-trifluoromethylphenyl | Cl |
| 181 | 3-methylpiperid-1-yl | 3-chlorophenyl | Cl |
| 182 | 3-methylpiperid-1-yl | phenyl | Cl |
| 183 | 3-methylpiperid-1-yl | 2-methylphenyl | Cl |
| 184 | 3-methylpiperid-1-yl | 4-methoxyphenyl | Cl |
| 185 | 3-methylpiperid-1-yl | 4-bromophenyl | Cl |
| 186 | 2-methylpiperid-1-yl | 3,4-difluorophenyl | Cl |
| 187 | 3-methylpiperid-1-yl | 3,4-difluorophenyl | Cl |
| 188 | 4-methylpiperid-1-yl | 3,4-difluorophenyl | Cl |
| 189 | azepan-1-yl | 3,4-difluorophenyl | Cl |
| 190 | 2-methylpiperid-1-yl | 2,6-dichlorophenyl | Cl |
| 191 | 3-methylpiperid-1-yl | 2,6-dichlorophenyl | Cl |
| 192 | 4-methylpiperid-1-yl | 2,6-dichlorophenyl | Cl |
| 193 | 2-methylpyrrolidin-1-yl | 2-chloro-6-fluorophenyl | Cl |
| 194 | 2-methylpyrrolidin-1-yl | 2,6-difluorophenyl | Cl |
| 195 | 2-methylpyrrolidin-1-yl | 2,6-dichlorophenyl | Cl |
| 196 | 2-methylpyrrolidin-1-yl | 2-chlorophenyl | Cl |
| 197 | 2-methylpyrrolidin-1-yl | 2-methylphenyl | Cl |
| 198 | 2-methylpyrrolidin-1-yl | 2-fluorophenyl | Cl |
| 199 | 2-methylpyrrolidin-1-yl | 3-fluorophenyl | Cl |
| 200 | 2-methylpiperid-1-yl | 2-fluorophenyl | Cl |
| 201 | 2-methylpiperid-1-yl | 3-fluorophenyl | Cl |
| 202 | 2-methylpiperid-1-yl | 3-methylphenyl | Cl |
| 203 | azepan-1-yl | 3-chloro-4-methoxyphenyl | Cl |
| 204 | 4-methylpiperid-1-yl | 3-chloro-4-methoxyphenyl | Cl |
| 205 | 3-methylpiperid-1-yl | 3-chloro-4-methoxyphenyl | Cl |
| 206 | pyrrolidin-1-yl | 3-chloro-4-methoxyphenyl | Cl |
| 207 | 2-methylpiperid-1-yl | 3-chloro-4-methoxyphenyl | Cl |
| 208 | 2-methylpiperid-1-yl | 4-tert-butylphenyl | Cl |
| 209 | 2-methylpiperid-1-yl | 3-trifluoromethylphenyl | Cl |
| 210 | 2-methylpiperid-1-yl | 2-chlorophenyl | Cl |
| 211 | 2-methylpiperid-1-yl | phenyl | Cl |
| 212 | 2-methylpiperid-1-yl | 4-methoxyphenyl | Cl |
| 213 | 2-methylpiperid-1-yl | 2-chloro-6-fluorophenyl | Cl |
| 214 | 4-(prop-2-yl)piperid-1-yl | 2-chloro-6-fluorophenyl | Cl |
| 215 | 4-methylpiperid-1-yl | 2-chloro-6-nitrophenyl | Cl |
| 216 | azepan-1-yl | 2-chloro-6-nitrophenyl | Cl |
| 217 | 2-methylpyrrolidin-1-yl | 2-chloro-6-nitrophenyl | Cl |
| 218 | piperid-1-yl | 2-chloro-6-nitrophenyl | Cl |

TABLE IIB

| Ex. No. | mp [°C.] | Ex. No. | mp [°C.] |
|---|---|---|---|
| 119 | 164 | 147 | 134 |
| 120 | 160 | 148 | 180 |
| 121 | 141 | 149 | 157 |
| 122 | 192 | 150 | 130 |
| 123 | 173–174 | 151 | 150 |
| 124 | 194–199 | 152 | 170 |
| 125 | 184–185 | 153 | 155 |
| 126 | 180–181 | 154 | 149–150 |
| 127 | 185–187 | 155 | 175 |
| 128 | 141–150 | 156 | 137–140 |
| 129 | 185–188 | 157 | 179–182 |
| 130 | 173–176 | 158 | 128–131 |
| 131 | 249–251 | 159 | 168–169 |
| 132 | 168–172 | 160 | 228–230 |
| 133 | 186–189 | 161 | 129–130 |
| 134 | 174–176 | 162 | 145–147 |
| 135 | 152–154 | 163 | 161–164 |
| 136 | 213–215 | 164 | 152–155 |
| 137 | 165–170 | 165 | 138–139 |
| 138 | 169–171 | 166 | 184 dec |
| 139 | 153–155 | 167 | 162–164 |
| 140 | 147–150 | 168 | 211–215 |
| 141 | 196–200 | 169 | 157–161 |
| 142 | 200–204 | 170 | 216–219 |
| 143 | 176 | 171 | 173–176 |
| 144 | 172–177 | 172 | 121–123 |
| 145 | 145–150 | 173 | 133–137 |
| 146 | 177 | 174 | 80 dec |
| 175 | 158–159 | 197 | 169 |
| 176 | 178–180 | 198 | 176 |
| 177 | 156 | 199 | 178 |
| 178 | 62–66 | 200 | 169 |
| 179 | 145–146 | 201 | 199–202 |
| 180 | 191 | 202 | 221–222 |
| 181 | 192–194 | 203 | 203–206 |
| 182 | 152–154 | 204 | 159–156 |
| 183 | 125 | 205 | 170–175 |
| 184 | 152 | 206 | 218–210 |
| 185 | 186 | 207 | 147–148 |
| 186 | 185–190 | 208 | 126–129 |
| 187 | 180 | 209 | 207–209 |
| 188 | 176 | 210 | 234–239 |
| 189 | 187 | 211 | 172–173 |
| 190 | 184–186 | 212 | 186–187 |
| 191 | 156–158 | 213 | 202–205 |
| 192 | 148 | 214 | 139 |
| 193 | 179 | 215 | 203–206 |
| 194 | 190 | 216 | 89–95 |
| 195 | 195 | 217 | 114 dec |
| 196 | 165 | 218 | 173–175 |

EXAMPLE 219

Fungicidal activity against *Venturia inaequalis* on Malus sp.

Apple cuttings of the variety Morgenduft, which are about 6 weeks old, were treated with a solution of the test compound (400 ppm) in water/acetone/Triton X or water/methanol/Triton X. After 24 hours, the plants were infected with a conidia suspension of *Venturia inaequalis* (about 50,000 conidia/ml), incubated in a dark climatic chamber at a relative humidity of 100% for 48 hours and then kept at a relative humidity of 95–99% and temperature of 18°–20° C. during the day and 13° C. during the night for about 14 days. The extent of infection was assessed according to the following scheme:

0=no infection
1=1–10% infection
2=11–40% infection
3=41–100% infection

The results of these tests are set out in Table II below:

TABLE II

| Example No. | Activity | Example No. | Activity |
|---|---|---|---|
| 1 | 1 | 28 | 2.3 |
| 2 | 0 | 29 | 1.8 |
| 3 | 2.5 | 30 | 1.3 |
| 4 | 2.3 | 31 | 2.3 |
| 7 | 1.8 | 32 | 0 |
| 8 | 1 | 33 | 0 |
| 9 | 1 | 34 | 1.5 |
| 11 | 2.8 | 37 | 1.3 |
| 12 | 1.3 | 38 | 0 |
| 13 | 2.3 | 39 | 1.0 |
| 14 | 2 | 40 | 1.0 |
| 15 | 2.7 | 41 | 0 |
| 16 | 2.7 | 43 | 0 |
| 17 | 0 | 46 | 1.0 |
| 19 | 2.4 | 47 | 2.8 |
| 20 | 3 | 48 | 2.9 |
| 21 | 1.4 | 49 | 2.9 |
| 22 | 0 | 50 | 2.9 |
| 23 | 2.5 | 51 | 2.5 |
| 24 | 3 | 52 | 2.8 |
| 25 | 1 | 55 | 2.5* |
| 27 | 2.5 | 56 | 1.5* |
| 57 | 1.5* | 80 | 0.8 |
| 58 | 2.3* | 81 | 2.3 |
| 59 | 1.8* | 82 | 2.3 |
| 60 | 1.5* | 83 | 1.6 |
| 61 | 0 | 86 | 1.3 |
| 62 | 0 | 87 | 0 |
| 63 | 0 | 88 | 0 |
| 64 | 0 | 91 | 2.0 |
| 70 | 0 | 105 | 0 |
| 71 | 1.3 | 106 | 0 |
| 73 | 2.8 | 107 | 0 |

*signifies concentration of test compound = 200 ppm.

EXAMPLE 220

Determination of MIC-Values of compounds against various phytopathogenic fungi

The MIC (Minimum Inhibition Concentration)-values were determined by serial dilution tests using 48-well microtitre plates. The dilution of the test compounds in the nutrient solution and the distribution to the wells were carried out by a TECAN RSP 5000 robotic processor.

The compounds were diluted to the following concentrations: 100, 50, 25, 12.5, 6.25, 3.13, 1.56, 0.78, 0.39, 0.20, 0.10 and 0.05 µg/ml.

For preparation of the nutrient solution, V8 juice (Trade Mark) was neutralized with calcium carbonate and centrifuged. The supernatant was diluted with distilled water (1:5) to the final concentration.

The fungi (*Alternaria solani*, *Botrytis cinerea*, *Septoria nodorum*) were added into the wells as a droplet of spore suspension. The microtitre plates were then incubated at 20° C. for 6–8 days. This MIC-value was determined by visual inspection of the plates. In the case of *Alternaria solani* and *Botrytis cinerea*, the lowest concentration in the dilution series without mycelial growth was defined to be the MIC-value. For *Spetoria nodorum*, no MIC-value but only a strong inhibition of growth was regularly observed.

The results of these tests are set out in Table III below:

TABLE III

| Example No. | MIC-value (µg/ml) | | |
|---|---|---|---|
| | Botrytis cinerea | Alternaria solani | Septoria nodorum |
| 1 | 12.5 | 1.56 | |
| 6 | 6.25 | 3.13 | |
| 7 | 25.0 | | |
| 8 | 6.25 | | |
| 9 | 3.13 | | |
| 10 | | 12.5 | |
| 18 | >100.0 | | |
| 19 | 50.0 | >100.0 | |
| 20 | 100.0 | 100.0 | |
| 21 | 12.5 | 25.0 | |
| 22 | 1.56 | 0.39 | >12.5 |
| 24 | >100.0 | | |
| 25 | 6.25 | 0.78 | >3.13 |
| 26 | 50.0 | | |
| 28 | | | >12.5 |
| 29 | | | >3.13 |
| 32 | 0.78 | 0.39 | >0.39 |
| 33 | 6.25 | 1.56 | >3.13 |
| 35 | 50.0 | | |
| 36 | >100.0 | | |
| 37 | | 0.78 | |
| 38 | 12.50 | 25.00 | |
| 39 | 25.00 | 0.39 | |
| 40 | 3.13 | 0.78 | |
| 41 | 25.00 | 12.50 | |
| 43 | 6.25 | 12.50 | |
| 46 | 12.50 | 12.50 | |
| 63 | 6.25 | 0.05 | |
| 64 | 3.13 | 0.05 | |
| 65 | | 3.13 | |
| 70 | 3.13 | 0.20 | |
| 71 | | 3.13 | |
| 73 | | 1.56 | |
| 82 | 12.50 | 3.13 | |
| 83 | 6.25 | 1.56 | |
| 85 | | 6.25 | |
| 86 | 25.00 | 1.56 | |
| 87 | | 12.50 | |
| 88 | | 12.50 | |
| 91 | | 12.50 | |
| 94 | | 1.56 | |
| 98 | 25.00 | | |
| 99 | 12.50 | | |
| 103 | | 25.00 | |
| 104 | | 25.00 | |
| 105 | 1.56 | 0.39 | |
| 106 | 3.13 | 3.13 | |
| 107 | 3.13 | 0.39 | |
| 110 | 25.00 | 12.50 | |
| 111 | 0.39 | 3.13 | |
| 112 | 3.13 | | |
| 113 | 3.13 | | |
| 114 | 1.56 | 12.50 | |
| 115 | 12.50 | 12.50 | |
| 116 | 25.00 | 3.13 | |
| 117 | 6.25 | 3.13 | |

EXAMPLE 221

The fungicidal activity of compounds of the invention was investigated by means of the following tests.
(a) Direct protectant activity against tomato late blight (*Phytophthora infestans*: PIP)

The test is a direct protectant one using a foliar spray. The upper leaf surfaces of tomato plants with two expanded leaves (cv. First in the field) are sprayed with a solution of test compound in 1:1 water/acetone containing 0.04% "TWEEN 20" (Trade Mark; a polyoxyethylene sorbitan ester surfactant). Plants are treated using an automated sprayline with an atomizing nozzle. The concentration of the compound is 1000 ppm, and the spray volume is 700 1/ha. After a subsequent period of 24 hours under normal glasshouse conditions, the upper surfaces of the leaves are inoculated by spraying with an aqueous suspension containing $2 \times 10^5$ zoospores/ml. The inoculated plants are kept for 24 hours in a high humidity cabinet and 5 days under growth chamber conditions. The assessment is based on the percentage of diseased leaf area compared with that on control leaves.

(b) Direct protectant activity against vine downy mildew (*Plasmopara viticola*: PVP)

The test is a direct protectant one using a foliar spray. The lower surface of leaves of whole vine plants (cv Cabernet Sauvignon) are sprayed with the test compound at a dosage of 1000 ppm using an automated sprayline as described under (a), and after a subsequent period of 24 hours under normal glasshouse conditions the lower surfaces of the leaves are inoculated by spraying with an aqueous suspension containing $2.5 \times 10^4$ zoosporangia/ml. The inoculated plants are kept for 24 hours in a high humidity cabinet, 5 days under normal glasshouse conditions and then returned for a further 24 hours to high humidity. Assessment is based on the percentage of leaf area covered by sporulation compared with that on control leaves.

(c) Activity against tomato early blight (*Alternaria solani*; AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20"—Trade Mark). One day after treatment the seedlings are inoculated by spraying the leaf upper surfaces with a suspension of *A. solani* conidia containing $10^4$ spores/ml. For 4 days after inoculation plants are kept moist in a humidity compartment at 21° C. Disease is assessed 4 days after inoculation, based on the percentage of leaf surface area covered by lesions.

(d) Direct protectant activity against broad bean grey mould (*Botrytis cinerea*; BCB)

The test is a direct protectant one using a foliar spray. The upper surfaces of leaves of broad bean plants (cv The Sutton) are sprayed with the test compound at a dosage of 1000 ppm using an automated sprayline as described under (a). 24 hours after spraying the leaves are inoculated with an aqueous suspension containing $10^5$ conidia/ml. For 4 days after inoculation plants are kept moist in a humidity compartment at 21° C. Disease is assessed 4 days after inoculation, based on the percentage of leaf surface area covered by lesions.

(e) Activity against wheat leafspot (*Leptosphaeria nodorum*; LN.)

The test is a direct therapeutic one, using a foliar spray. Leaves of wheat plants (cv Norman), at the single leaf stage, are inoculated by spraying with an aqueous suspension containing $1 \times 10^6$ spores/ml. The inoculated plants are kept for 24 hours in a high humidity compartment prior to treatment. The plants are sprayed with a solution of the test compound at a dosage of 1000 ppm using an automated sprayline as described under (a). After drying, the plants are kept for 6–8 days at 22° C. and moderate humidity, followed by assessment. Assessment is based on the density of lesions per leaf compared with that on leaves of control plants.

(f) Activity against wheat brown rust (*Puccinia recondita*; PR)

The test is a direct protectant one using a foliar spray. Wheat seedlings (cv Avalon) are grown to the 1–1½ leaf stage. The plants are then sprayed with the test compound at a dosage of 1000 ppm using an automated sprayline as described under (a). Test compounds are applied as solutions or suspensions in a mixture of acetone and water (50:50 v/v) containing 0.04% surfactant ("TWEEN 20"—Trade Mark). 18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°–22° C. Thereafter, the plants are kept in ambient glasshouse conditions, that is, in moderate relative humidity and at a temperature of 20°C. The disease is assessed 10 days after inoculation on the basis of the percentage of the plant covered by sporulating pustules compared with that on the control plants.

g) Activity against barley powdery mildew (*Erysiphe graminis* f.sp hordei; EG)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1000 ppm using an automated sprayline as described under (a). After drying, plants are returned to a compartment at 20°–25° C. and moderate humidity for up to 7 days, followed by assessment. Assessment is based on the percentage of leaf area covered by sporulation compared with that on leaves of control plants.

(h) Activity against rice leaf blast (*Pyricularia oryzae*; PO)

The test is a direct therapeutic one using a foliar spray. The leaves of rice seedlings (cv Aichiaishi—about 30 seedlings per pot) are sprayed with an aqueous suspension containing $10^5$ spores/ml 20–24 hours prior to treatment with the test compound. The inoculated plants are kept overnight in high humidity and then allowed to dry before spraying with the test compound at a dosage of 1000 ppm using an automated sprayline as described under (a). After treatment the plants are kept in a rice compartment at 25°–30° C. and high humidity. Assessments are made 4–5 days after treatment and are based on the density of necrotic lesions per leaf when compared with control plants.

(i) Activity against wheat eyespot in-vitro (*Pseudocercosporella herpotrichoides*; PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 50 ppm compound and 2.5% acetone. Each compartment is inoculated with a 6 mm diameter plug of agar/mycelium taken from a 14 day old culture of *P. herpotrichoides*.

Plates are incubated at 20° C. for 12 days until the assessment of mycelial growth.

(j) Activity against Fusarium in-vitro (*Fusarium culmorum*; FSI)

This test measures the in vitro activity of compounds against a species of Fusarium that causes stem and root rots. The test compound is dissolved or suspended in acetone and added to molten half strength Potato Dextrose Agar to give a final concentration of 50 ppm compound and 2.5% acetone. After agar has set, plates are inoculated with 6 mm diameter plugs of agar and mycelium taken from a 7 day old culture of Fusarium sp. Plates are incubated at 20° C. for 5 days and radial growth from the plug is measured.

(k) Activity against Rhizoctonia in vitro (*Rhizoctonia solani*: RSI)

This test measures the in vitro activity of compounds against *Rhizoctonia solani*, a fungus that causes stem and root rot. The test compound is dissolved or suspended in acetone and added into aliquots of 4 ml half strength Potato Dextrose Broth dispensed in 25-compartment petri dishes to give a final concentration of 50 ppm compound and 2.5% acetone.

The fungal inoculum consists of mycelial fragments of *R. solani* grown in shaken culture flasks and added to the broth to provide $2 \times 10^3$ fragments/ml broth.

Plates are incubated at 20° C. for 10 days until the assessment of mycelial growth.

The extent of disease control in all the above tests is expressed as a rating compared with either an untreated control or a diluent-sprayed-control, according to the criteria:

0=less than 50% disease control

1=about 50–80% disease control

2=greater than 80% disease control

The results of these tests are set out in Table IV below:

20° C. and 40% relative humidity. Infected leaves are sprayed on their lower surfaces with a solution of the test compound in 1:1 water/acetone containing 0.04% "TWEEN 20" (Trade Mark; a polyoxyethylene sorbitan ester surfactant). Plants are sprayed using a track sprayer equipped with 2 air-atomizing nozzles. The concentration of the compound is 600 ppm and the spray volume is 750 l/ha. After drying, the plants are returned to the glasshouse at 20° C. and 40% relative humidity for 96 hours and are then transferred to the high humidity cabinet for 24 hours to induce sporulation. Assessment is based on the percentage of the leaf area covered by sporulation compared with that on control leaves.

(b) Direct protectant activity against tomato late blight (*Phytophthora infestans*; PIP)

The test is a direct protectant one using a foliar spray. Tomato plants with two expanded leaves (cv. First in the Field) are sprayed with the test compound at a dosage of 600 ppm as described under (a). After drying, the plants are kept for 24 hours in a glasshouse at 20° C. and 40% relative humidity. The upper surfaces of the leaves are then inoculated with an aqueous suspension containing $2 \times 10^5$ zoosporangia/ml. The inoculated plants are kept for 24 hours at 18°

TABLE IV

| Ex. No. | Fungicidal Activity | | | | | | | | | | |
|---|---|---|---|---|---|---|---|---|---|---|---|
| | PIP | PVP | AS | BCB | LN | PR | EG | PO | PHI | FSI | RSI |
| 10 | | 1 | 2 | 1 | | | 1 | | | | |
| 34 | | | | 2 | | | | | | | |
| 37 | | | 2 | | | 2 | 1 | | | 1 | |
| 38 | 1 | | | 2 | | 2 | 2 | | | 1 | |
| 39 | 1 | | 2 | 2 | | | | | | | |
| 40 | | | 2 | 2 | | | 2 | | 1 | | 2 |
| 41 | | | 2 | 2 | 2 | | 2 | 2 | 1 | | 2 |
| 42 | | | | 2 | | 1 | | | | 1 | |
| 43 | | | 2 | 2 | | 1 | 2 | 2 | 1 | | |
| 44 | | | | 2 | | 1 | | | 1 | | |
| 53 | | 1 | 2 | 1 | | | | | | | |
| 54 | | | 1 | | | | | | | | |
| 65 | | | 2 | 1 | | | | | | | |
| 66 | | | | 2 | | 1 | 1 | | 1 | 1 | |
| 67 | | | 2 | | | | | | 2 | | |
| 68 | | | 2 | | | 2 | | | | | |
| 69 | | | | | | | 1 | | | | |
| 70 | | | 2 | 2 | | 1 | | | 2 | 1 | |
| 71 | | | 2 | 1 | | 2 | 1 | | 2 | | |
| 72 | | | | | | 2 | | | | | |
| 73 | | | 2 | | | | | | | | |
| 74 | | | | | | 1 | | | | | |
| 75 | | | | | | 1 | | | | | |
| 76 | | | | | | 1 | | | | | |
| 77 | | | 2 | 1 | | 1 | | | | | |
| 78 | | | 2 | 2 | | 1 | | | | | |
| 79 | | | 1 | 1 | | | | | | | |
| 82 | | | 2 | 2 | | | | | 2 | | 2 |
| 84 | | | | | | | | | | | 1 |
| 85 | | | 2 | 1 | | | | | 1 | | |
| 86 | | | 1 | | | | | | 1 | | |

EXAMPLE 222

The fungicidal activity of compounds of the invention was investigated by means of the following tests.

(a) Antisporulant activity against vine downy mildew (*Plasmopara viticola*; PVA)

The test is a direct antisporulant one using a foliar spray. The lower surface of leaves of vine plants (cv. Cabernet Sauvignon), approximately 8 cm high, are inoculated with an aqueous suspension containing $5 \times 10^4$ zoosporangia/ml. The inoculated plants are kept for 24 hours at 21° C. in a high humidity cabinet, then for 24 hours in a glasshouse at C. in a high humidity cabinet and then for 5 days in a growth chamber at 15° C. and 80% relative humidity with 14 hours light/day. The assessment is based on the percentage of diseased leaf area compared with that on control leaves.

(c) Activity against tomato early blight (*Alternaria solani*; AS)

The test is a direct prophylactic one using a foliar spray. Tomato seedlings (cv Outdoor Girl), at the stage at which the second leaf is expanded, are sprayed with the test compound at a dosage of 600 ppm as described under (a). After drying, the plants are kept for 24 hours in a glasshouse at 20° C. and 40% relative humidity followed by inoculation of the leaf upper surfaces with an aqueous suspension of *A. solani* conidia containing 1×10 conidia/ml. After 4 days in a high humidity cabinet at 21° C., disease is assessed based on the percentage of leaf surface area covered by lesions when compared with control plants.

(d) Direct protectant activity against broad bean grey mould (*Botrytis cinerea*; BCB)

The test is a direct protectant one using a foliar spray. Broad bean plants (cv The Sutton) with two leaf pairs are sprayed with the test compound at a dosage of 600 ppm as described under (a). After drying, the plants are kept for 24 hours in a glasshouse at 20° C. and 40% relative humidity. The upper surface of the leaves are then inoculated with an aqueous suspension containing 1×10$^6$ conidia/ml. Plants are kept for 4 days at 22° C. in a high humidity cabinet. The assessment is based on the percentage of diseased leaf area compared with that on control leaves.

(e) Activity against barley Powdery mildew (*Erysiphe graminis* f.sp. hordei: EG)

The test is a direct therapeutic one using a foliar spray. Leaves of barley seedlings (cv Golden Promise) at the single leaf stage are inoculated by dusting with mildew conidia and kept in the glasshouse at 18° C. and 40% relative humidity for 24 hours. Plants are then sprayed with the test compound at a dosage of 600 ppm as described under (a). After drying, plants are returned to the glasshouse at 18° C. and 40% relative humidity for up to 7 days. Assessment is based on the percentage of leaf area covered by sporulation compared with that on leaves of control plants.

(f) Activity against rice leaf blast (*Pyricularia oryzae*; PO)

The test is a direct therapeutic one using a foliar spray. The leaves of rice seedlings at the stage of the second leaf beginning to bend (cv Aichiaishi) are inoculated with an aqueous suspension containing 10$^5$ spores/ml. The inoculated plants are kept for 24 hours at 18° C. in a high humidity cabinet and then sprayed with the test compound at a dosage of 600 ppm as described under (a). Treated plants are kept for 8–9 days in the glasshouse at 22° C. and 90% relative humidity. Assessment is based on the density of necrotic lesions when compared with control plants.

(g) Activity against wheat eyespot in vitro (*Pseudocercosporella herpotrichoides*; PHI)

This test measures the in vitro activity of compounds against the fungus causing wheat eyespot. The test compound is dissolved or suspended in acetone and is added into 4 ml aliquots of half strength Potato Dextrose Broth dispensed in 25-compartment petri dishes to give a final concentration of 10 ppm test compound and 0.825% acetone. The fungal inoculum consists of mycelial fragments of *P. herpotrichoides* grown in half strength Potato Dextrose Broth in shaken flasks and added to the broth to provide 5×10$^4$ mycelial fragments/ml broth. Petri dishes are incubated at 20° C. for 10 days until the assessment of mycelial growth.

h) Activity against Rhizoctonia in vitro (*Rhizoctonia solani*: RSI)

The test measures the in vitro activity of compounds against *Rhizoctonia solani* which causes stem and root rot. The test compound is dissolved or suspended in acetone and added into 4 ml aliquots of half strength Potato Dextrose Broth dispensed in 25-compartment petri dishes to give a final concentration of 10 ppm compound and 0.825% acetone. The fungal inoculum consists of mycelial fragments of *R. solani* grown in half strength Potato Dextrose Broth in shaken culture flasks and added to the broth to provide 5×10$^4$ fragments/ml broth. Petri dishes are incubated at 20° C. for 10 days until the assessment of mycelial growth.

(i) Activity against apple scab in vitro (*Venturia inaequalis*; VII)

This test measures the in vitro activity of compounds against *Venturia inaequalis* which causes apple scab. The test compound is dissolved or suspended in acetone and added into 4 ml aliquots of half strength Potato Dextrose Broth dispensed in 25-compartment petri dishes to give a final concentration of 10 ppm compound and 0.825% acetone. The fungal inoculum consists of mycelial fragments and spores of *V. inaequalis* grown on malt agar and added to the broth to provide 5×10$^4$ propagules/ml broth. Petri dishes are incubated at 20° C. for 10 days until the assessment of mycelial growth.

The extent of disease control in all the above tests is expressed as a rating compared with either an untreated control or a diluent-sprayed-control, according to the criteria:

0=less than 50% disease control

1=50–80% disease control

2=greater than 80% disease control

The results of these tests are set out in Table V below:

TABLE V

| Example No. | Fungicidal Activity | | | | | | | | |
|---|---|---|---|---|---|---|---|---|---|
| | PVA | PIP | AS | BCB | EG | PO | PHI | RSI | VII |
| 45 | | | | | | | | | 2** |
| 89 | | | 1 | 1 | | | | | 1* |
| 90 | | 1 | 2 | | | | | | 1* |
| 92 | 1 | | | | | 1 | | | |
| 93 | | 2 | | | | | | | |
| 94 | | | 2 | | | | | 1 | 2 |
| 95 | | | 2 | | | | | 1 | 2 |
| 96 | | | 2 | | | | | | 2 |
| 97 | | 2 | | | | | | | |
| 98 | | 2 | 2 | 1 | | | | 1 | 1 |
| 99 | | 2 | 2 | 2 | 1 | | | 2 | 2 |
| 100 | | 2 | | | | | | | |
| 101 | | | | 2 | | | | 1 | |
| 102 | | 2 | 2 | | 1 | | | 1 | 2 |
| 106 | | 2 | 2 | 2 | 2 | 1 | 1 | 2 | 1 |
| 107 | | 2 | 2 | 2 | 2 | | 1 | 2 | 1 |
| 108 | | 2 | | | | | | | |
| 109 | | 2 | 2 | 2 | 1 | | | 2 | |

*signifies dosage of test compound = 30 ppm
**signifies dosage of test compound = 3 ppm Example 223

Determination of Effective Dose for >90% Inhibition by Test Compounds in the Serial Dilution Test with Various Phytopathogenic Fungi The ED>90 (Effective lose >90%)-value is determined by serial dilution tests using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.05, 0.10, 0.20, 0.39, 0.78, 1.56, 3.13, 6.25, 12.50, 25.00, 50.00 and 100.00 mg/ml. For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The respective inocula (*Alternaria solani*, ALTESO; *Botrytis cinerea*, BOTRICI; *Cercospora beticola*, CERCBE; *Cladosporium herbarum*, MYCOTA; *Corticium rolfsii*, SCLORO; *Helminthosporium tritici repentis*, PYRNTR; *Leptosphaeria nodorum*, LEPTNO; *Micronectriella nivalis*, MICNI; *Monilinia fructigena*, MONIFG; *Mycosphaerella ligulicola*, MYCOLG; *Mycosphaerella pinodes*, MYCOPI; *Rhizoctonia solani*, RHYZSO; *Sclerotinia sclerotiorum*, SCLESC) are added into the wells as spore suspensions (50 ml; 5×10⁵ ml) or agar slices (6 mm) of an agar culture of the fungus.

After 6–12 days incubation at suitable temperatures (18°–25° C.), the ED>90 values are determined by visual inspection of the plates. The lowest concentration in the dilution series with mycelial growth of less than 10% is defined to be the ED>90 value (Table VIA-C).

TABLE VIA

| Ex. No. | ALTESO | BOTRCI | CERCBE | MY-COTA | PYRNTR |
|---|---|---|---|---|---|
| 118 | 0.05 | 0.15 | 0.10 | 0.05 | 0.39 |
| 119 | 1.56 | 0.39 | | | |
| 120 | 0.78 | 3.13 | 0.78 | 50.00 | 6.25 |
| 121 | 0.39 | 0.78 | 0.78 | 0.78 | 3.13 |
| 122 | 0.20 | 12.50 | | | |
| 123 | 12.50 | >100 | | | |
| 124 | 50.00 | 50.00 | | | |
| 125 | 0.20 | 3.13 | | | |
| 126 | 0.39 | 12.50 | | | |
| 127 | 3.13 | 6.25 | | | |
| 129 | 0.39 | 0.78 | | | |
| 130 | 3.13 | 3.13 | | | |
| 131 | 3.13 | 6.25 | | | |
| 132 | 1.56 | 1.56 | | | |
| 133 | 0.20 | 0.88 | | | |
| 134 | 0.10 | 0.30 | 1.56 | | 1.56 |
| 135 | 0.65 | 1.45 | 6.25 | >100 | 100.00 |
| 136 | 0.12 | 1.43 | 0.20 | | >100 |
| 137 | 0.52 | 0.78 | 3.13 | 1.56 | 100.00 |
| 138 | 0.59 | 0.59 | 3.13 | >100 | 100.00 |
| 139 | 0.05 | 0.15 | 0.78 | 0.05 | 0.39 |
| 140 | 0.25 | 0.25 | 3.13 | 0.39 | 1.56 |
| 141 | >100 | 3.13 | | | |
| 142 | 6.25 | 25.00 | | | |
| 143 | 0.20 | 1.17 | 3.13 | | 25.00 |
| 144 | 3.52 | >100 | | >100 | |
| 145 | 0.10 | 3.13 | | | |
| 147 | 2.35 | 18.75 | 1.56 | >100 | 25.00 |
| 148 | 100.00 | >100 | | | |
| 149 | >100 | >100 | | | |
| 150 | 0.78 | 0.78 | | | |
| 151 | 0.15 | 0.49 | 0.78 | 0.20 | 3.13 |
| 152 | 6.25 | 12.50 | | | |
| 153 | >100 | >100 | | | |
| 154 | 0.10 | 0.39 | | | |
| 155 | 0.78 | 100.00 | | | |
| 156 | 0.20 | 0.39 | | | |
| 157 | >100 | 1.56 | | | |
| 158 | >100 | >100 | | | |
| 159 | 3.13 | 100.00 | | | |
| 160 | 50.00 | >100 | | | |

TABLE VIA-continued

| Ex. No. | ALTESO | BOTRCI | CERCBE | MY-COTA | PYRNTR |
|---|---|---|---|---|---|
| 161 | 3.13 | 50.00 | | | |
| 162 | 0.10 | 0.39 | | | |
| 163 | 0.20 | 0.20 | | | |
| 164 | 0.05 | 0.20 | | | |
| 165 | 0.10 | 0.20 | | | |
| 166 | >100 | >100 | | | |
| 167 | 0.78 | 50.00 | | | |
| 168 | >100 | >100 | | | |
| 169 | 6.25 | 25.00 | | | |
| 170 | 50.00 | >100 | | | |
| 171 | 0.20 | 1.56 | | | |
| 172 | 0.20 | 0.05 | | | |
| 173 | >100 | >100 | | | |
| 174 | 3.13 | 50.00 | | | |
| 175 | 0.05 | 0.39 | | | |
| 176 | 12.50 | >100 | | | |
| 177 | 0.05 | 0.20 | | | |
| 178 | 12.50 | 12.50 | | | |
| 179 | >100 | >100 | | | |
| 180 | >100 | >100 | | | |
| 181 | >100 | >100 | | | |
| 182 | 25.00 | >100 | | | |
| 183 | 3.13 | 25.00 | | | |
| 184 | 1.56 | >100 | | | |
| 185 | >100 | >100 | | | |
| 186 | >100 | >100 | | | |
| 187 | >100 | >100 | | | |
| 188 | 0.78 | >100 | | | |
| 189 | 0.78 | >100 | | | |
| 190 | 0.20 | 0.39 | | | |
| 191 | 0.78 | >100 | | | |
| 192 | 0.20 | 0.78 | | | |
| 193 | 0.39 | 0.39 | | | |
| 194 | 0.39 | 1.56 | | | |
| 195 | >100 | >100 | | | |
| 196 | 1.56 | 3.13 | | | |
| 197 | 3.13 | 6.25 | | | |
| 198 | 1.56 | 6.25 | | | |
| 199 | 25.00 | 3.13 | | | |
| 200 | 1.56 | 12.50 | | | |
| 201 | >100 | >100 | | | |
| 202 | >100 | >100 | | | |
| 203 | >100 | >100 | | | |
| 204 | 3.13 | 25.00 | | | |
| 205 | >100 | >100 | | | |
| 206 | >100 | >100 | | | |
| 208 | >100 | >100 | | | |
| 209 | >100 | >100 | | | |
| 210 | >100 | >100 | | | |
| 211 | >100 | >100 | | | |
| 212 | 3.13 | 3.13 | | | |
| 213 | 0.78 | >100 | | | |
| 214 | 0.39 | 3.13 | | | |
| 215 | 3.13 | 6.25 | | | |

TABLE VIB

| Ex. No. | LEPTNO | MICNNI | MONIFG | MYCOLG | MYCOPI | SCLSCE |
|---|---|---|---|---|---|---|
| 118 | 0.78 | 0.78 | 0.10 | 0.05 | >100 | 100.00 |
| 120 | 3.13 | 3.13 | 1.56 | 0.39 | 3.13 | 100.00 |
| 121 | 25.00 | 0.20 | 0.39 | 0.78 | 0.39 | 3.13 |
| 134 | >100 | 3.13 | 0.39 | 0.39 | 3.13 | 25.00 |
| 135 | 3.13 | 6.15 | 1.56 | 3.13 | 12.50 | 50.00 |
| 136 | 25.00 | 12.50 | 0.78 | 0.20 | 25.00 | >100 |
| 137 | 0.78 | 6.25 | 0.78 | 1.56 | 3.13 | 100.00 |
| 138 | 3.13 | 0.20 | 0.78 | 0.78 | 3.13 | >100 |
| 139 | 0.78 | 3.13 | 0.20 | 0.10 | 0.78 | 1.56 |
| 140 | 1.56 | 1.56 | 0.39 | 0.39 | 0.05 | 25.00 |
| 143 | 50.00 | 100.00 | 3.13 | 3.13 | 3.13 | 6.25 |
| 144 | >100 |  |  | >100 |  | >100 |
| 147 | 50.00 | 100.00 | 3.13 | 3.13 | 3.13 | >100 |
| 151 | 0.78 | 3.13 | 0.20 | 0.39 | 0.78 | >100 |
| 213 | 6.25 | 6.25 |  |  |  |  |

TABLE VIC

| Ex. No. | RHIZSO | SCLORO | Ex. No. | RHIZSO | SCLORO |
|---|---|---|---|---|---|
| 118 | 1.67 | 0.39 | 147 | >100 | 25.00 |
| 120 | 25.00 | 3.13 | 148 | >100 |  |
| 121 | 0.78 | 3.13 | 149 | >100 |  |
| 122 | >100 |  | 151 | 1.56 | 0.39 |
| 123 | >100 |  | 154 | 0.39 |  |
| 124 | >100 |  | 155 | >100 |  |
| 125 | 0.78 |  | 156 | 3.13 |  |
| 126 | 12.50 |  | 157 | >100 |  |
| 127 | >100 |  | 158 | >100 |  |
| 129 | 3.13 |  | 159 | 100.00 |  |
| 130 | 6.25 |  | 160 | >100 |  |
| 131 | >100 |  | 161 | >100 |  |
| 132 | 12.50 |  | 162 | 3.13 |  |
| 133 | >100 |  | 163 | 3.13 |  |
| 134 | 3.13 | 1.56 | 164 | 6.25 |  |
| 135 | >100 | 6.25 | 165 | 1.56 |  |
| 136 | >100 | >100 | 166 | >100 |  |
| 137 | 37.50 | 25.00 | 167 | >100 |  |
| 138 | >100 | 100.00 | 168 | >100 |  |
| 139 | 1.17 | 0.39 | 169 | >100 |  |
| 140 | 0.59 | 1.56 | 170 | >100 |  |
| 141 | >100 |  | 171 | 12.50 |  |
| 142 | >100 |  | 172 | 0.78 |  |
| 143 | >100 | 3.13 | 173 | >100 |  |
| 144 | >100 |  | 174 | >100 |  |
| 145 | 1.56 |  | 175 | 6.25 |  |
| 176 | >100 |  | 196 | 12.50 |  |
| 177 | 3.13 |  | 197 | 12.50 |  |
| 178 | >100 |  | 198 | 25.00 |  |
| 179 | >100 |  | 199 | 6.25 |  |
| 180 | >100 |  | 200 | >100 |  |
| 181 | >100 |  | 201 | >100 |  |
| 182 | >100 |  | 202 | >100 |  |
| 183 | >100 |  | 203 | >100 |  |
| 184 | >100 |  | 204 | >100 |  |
| 185 | >100 |  | 205 | >100 |  |
| 186 | >100 |  | 206 | >100 |  |
| 187 | >100 |  | 207 | >100 |  |
| 188 | >100 |  | 208 | >100 |  |
| 189 | >100 |  | 209 | >100 |  |
| 190 | 3.13 |  | 210 | >100 |  |
| 191 | >100 |  | 211 | >100 |  |
| 192 | >100 |  | 212 | >100 |  |
| 193 | 3.13 |  | 213 | >100 |  |
| 194 | 0.78 |  | 214 | >100 |  |
| 195 | >100 |  | 215 | >100 |  |

EXAMPLE 224

Determination of Activity of Test Compounds Against Cereal Powdery Mildew

This test measures the prophylactic activity of test compounds applied as a foliar spray. Cereal seedlings (barley, cv Golden promise; wheat, cv Kormoran) are grown to the 1 leaf stage. The plants are then sprayed with a solution of active material in water, made up from a 5000 ppm stock solution in acetone containing 5000 ppm of TRITON™ X 155 (a non-ionic polyoxyethylene ether surfactant). Plants are treated using an automated sprayline with an atomising nozzle. The spray volume is 20 ml. 24 hours after treatment the seedlings are inoculated with powdery mildew by shaking stock culture plants with sporulating pathogen (barley—*Erysiphe graminis* f.sp. hordei; wheat—*Erysiphe graminis* f.sp. tritici) over them. Thereafter, the plants are kept for 3 h without air movement in order to allow the spores to settle on the leaves. The plants are then kept in the greenhouse until symptoms occur. Assessment is based on the percentage of diseased leaf area compared with that on control leaves (Table VII).

TABLE VII

| | Activity [%] | |
|---|---|---|
| Ex. No. | Barley 100 ppm | Wheat 100 ppm |
| 118 | 100 | 91 |
| 139 | 100 | 100 |
| 140 | 100 | 44 |

EXAMPLE 225

Determination of Activity of Test Compounds Against Rice Blast (*Pyricularia oryzae*)

This test measures the protectant activity of test compounds upon foliar application. Rice seedlings (*Oryza sativa* L. "M-9") are grown in the greenhouse. Approximately two weeks after seeding, the plants are sprayed with a solution of active material (200 ppm) in a solvent/surfactant system containing 5% aceton and 0.05% TWEEN™ 20 (a polyoxyethylenesorbitan monolaurate surfactant) in deionized water. All foliar surfaces of the plants are sprayed to the point of run-off, and the plants are allowed to air-dry 2–5 hours prior to inoculation. The inoculate is prepared from *Pyricularia oryzae* Cavara (culture FD 7, FD 190) (PYRIOR) grown on oatmeal agar plates, of which the conidia are washed off with a solution of 0.05% TWEEN 20 in deionized water. Then the conidia concentration is adjusted to 1,000,000 conidia/ml. This solution is used for inoculating the foliage, including the clams, by spraying the conidia suspension onto the plants. Thereafter the plants are kept in a moisture chamber (18°–28° C., 100% rel. humidity) for 24–48 hours. Thereafter, the plants are placed in th greenhouse for 8–10 days. Assessment is based on the percentage of diseased leaf area compared with that on leaves of control plants. The activity is expressed as percentage of disease control using the rating scale shown below.

RATING SCALE

| Rating | % Disease Control |
|---|---|
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |

TABLE VIII

| Ex. No. | PYRIOR | Ex. No. | PYRIOR |
|---|---|---|---|
| 118 | 0 | 130 | 0 |
| 119 | 8 | 131 | 0 |
| 120 | 8 | 132 | 0 |
| 121 | 9 | 133 | 4 |
| 122 | 0 | 134 | 0 |
| 124 | 0 | 135 | 0 |
| 125 | 7 | 136 | 0 |
| 126 | 0 | 137 | 7 |
| 127 | 5 | 138 | 5 |
| 128 | 3 | 139 | 8 |
| 129 | 0 | 140 | 6 |
| 141 | 0 | 171 | 7 |
| 142 | 0 | 172 | 8 |
| 143 | 3 | 173 | 0 |
| 144 | 6 | 174 | 0 |
| 145 | 2 | 175 | 3 |
| 147 | 0 | 176 | 0 |
| 148 | 5 | 177 | 7 |
| 149 | 0 | 178 | 7 |
| 150 | 7 | 179 | 2 |
| 151 | 0 | 180 | 0 |
| 152 | 6 | 181 | 0 |
| 153 | 3 | 184 | 5 |
| 154 | 7 | 185 | 0 |
| 155 | 0 | 186 | 0 |
| 156 | 0 | 187 | 0 |
| 157 | 5 | 188 | 4 |
| 158 | 0 | 189 | 3 |
| 159 | 0 | 190 | 4 |
| 160 | 0 | 191 | 4 |
| 161 | 0 | 192 | 4 |
| 162 | 5 | 193 | 7 |
| 163 | 7 | 194 | 7 |
| 164 | 0 | 195 | 0 |
| 165 | 0 | 196 | 6 |
| 166 | 0 | 197 | 5 |
| 167 | 2 | 198 | 6 |
| 168 | 0 | 199 | 4 |
| 169 | 3 | 214 | 2 |
| 170 | 0 | 215 | 4 |

Example 226

Determination of Activity of Test Compounds in Field Trials Against Rice Blast

This test measures the curative effect of the test compounds. Rice (*Oryza sativa* var. Koshihikari) is grown in field plots (1 m×1 m; 1 m²). The plants are sprayed with the test compounds 8 and 20 days after inoculation with rice leaf blast (*Pyricularia oryzae*) and additional transplanting of infected seedlings. The spray volume is 0.1 l/plot, equivalent to 1,000 l/ha. Assessments of the results are carried out 11 days after the first (11 DAT1) and 15 days after the second application (15 DAT2). They are based on the percentage of diseased leaf area compared with that on leaves of control plants. The activity is expressed as percentage of disease control (Table IX).

TABLE IX

| Ex. No. | Dose [ppm] | % Control | |
|---|---|---|---|
| | | 11 DAT1 | 15 DAT2 |
| 118 | 200 | 73 | 80 |
| | 400 | 68 | 80 |
| 139 | 200 | 72 | 64 |
| | 400 | 64 | 59 |

Example 227

Activity Against Grapevine Powdery Mildew (*Uncinula necator*)

This test measures the direct protectant activity of test compositions and test compounds applied as foliar spray. Cuttings of grapevine (cv Müller-Thurgau) are grown to the 6–8 leaf stage and then cut back to 4 equally sized leaves. The plants are sprayed to run-off in a spray cabinet with a solution (20 ml, 200 ppm) of active material in water made up from a 5000 ppm stock solution in acetone containing 5000 ppm of TRITON® X 155. 48 hours after treatment the cuttings are inoculated with conidia of *Uncinula necator* (UNCINE) in a special spore setting tower. The spores are blown from freshly sporulating grape leaves (*U. necator* stock culture) into the upper hole of the settling tower and are allowed to settle on the leaves for 5 min. Then the plants are kept in a phytotron at 18° C. night and 22° C. day temperature at an interval of 12 h night and 12 h day. Illumination is accomplished by fluorescent tubes at 11,200 lux. Assessment is carried out after 21d by visual inspection and based on the percentage of the diseased leaf area of the three youngest leaves compared with that on control plants.

The results of the tests are set out in Table X below, in which the compounds are identified by reference to the preceding Example Nos. and to above. Absence of a numerical indicates that none of the tests described above is carried out. A rating 0 indicates disease as untreated control, a rating 100 indicates no infection.

Fungicidal activity against *Venturia inaequalis* on Malus sp.

Apple seedlings of the varieties Morgenduft or Macintosh, which are about 6 weeks old, are treated with a solution of the respective test compound (100 ppm) in water/aceton/ TRITON X or water/methanol/TRITON X. After 72 hours, the plants are infected with a conidia suspension of *Venturia inaequalis* (c. 50,000 conidia/ml) (VENTIN), incubated in a dark climatic chamber at a relative humidity of 100% for 48 h and, then, kept at a relative humidity of 95–99% and temperatures of 18°–20° C. during the day and 13° C. during the night for about 14 days.

The results of the tests are set out in Table X below, in which the compounds are identified by reference to the preceding Example Nos. and to above. Absence of a numerical indicates that none of the tests described above is carried out. A rating 0 indicates disease as untreated control, a rating 100 indicates no infection.

TABLE X

| Ex. No. | % Disease Control | |
| --- | --- | --- |
| | UNCINE | VENTIN |
| 118 | 100 | 94 |
| 119 | 100 | 96 |
| 120 | 83 | 86 |
| 125 | 91 | 48 |
| 129 | 72 | |
| 130 | 77 | |
| 131 | | 61 |
| 134 | 100 | |
| 137 | 100 | 80 |
| 138 | 97 | 36 |
| 139 | 100 | 88 |
| 140 | 100 | 60 |
| 143 | | 76 |
| 147 | | 57 |
| 151 | | 68 |
| 152 | | 42 |
| 154 | | 74 |
| 162 | | 37 |
| 163 | | 36 |
| 164 | | 91 |
| 165 | | 89 |
| 167 | | 36 |
| 171 | | 89 |
| 174 | | 54 |
| 175 | | 66 |
| 177 | | 89 |

We claim:
1. A fungicidal compound of formula I

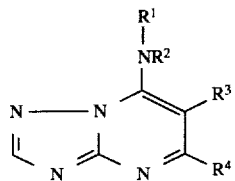

wherein

R$_1$ represents a C$_{1-12}$alkyl, C$_{2-6}$alkenyl, C$_{2-6}$alkynyl, C$_{4-12}$alkadienyl, C$_{3-8}$cycloalkyl, benzyl, furyl, or bicycloheptyl group optionally substituted by one to three substituents selected from the group consisting of halogen atoms, hydroxyl, C$_{1-4}$alkyl, C$_{1-4}$haloalkyl, C$_{1-4}$alkoxy, C$_{1-4}$haloalkoxy, carboxyl, phenyl and C$_{1-4}$alkoxycarbonyl, and R$_2$ represents a hydrogen atom or an alkyl group having 1–4 carbon atoms, or R$_1$ and R$_2$ together with the adjacent nitrogen atom represent a pyrrolidinyl, piperidyl, or dihydropyridyl ring optionally substituted by one or more C$_{1-4}$alkyl groups;

R$_3$ represents a phenyl or naphthyl group optionally substituted by one to three substituents selected from the group consisting of halogen atoms, hydroxyl, nitro, cyano, C$_{1-12}$alkyl, C$_{1-12}$haloalkyl, C$_{1-4}$alkoxy, C$_{1-12}$haloalkoxy, amino, C$_{1-4}$alkylamino, di-C$_{1-4}$alkylamino, formyl, carboxyl, phenyl, phenoxy, benzyloxy, and C$_{1-4}$alkoxycarbonyl; and R$_4$ represents a halogen atom or a group NR$_5$R$_6$ where R$_5$ represents a hydrogen atom or an amino, C$_{1-4}$alkyl, C$_{3-6}$cycloalkyl or bicycloheptyl group and R$_6$ represents a hydrogen atom or an C$_{1-4}$alkyl group.

2. The compound according to claim 1 wherein R$_1$ and R$_2$ are taken together with the interjacent nitrogen atom to represent a pyrrolidinyl, piperidyl, or dihydropyridyl, ring optionally substituted with one or more C$_{1-4}$alkyl group; R$_3$ represents a phenyl group optionally substituted with one to three C$_{1-4}$alkyl, C$_{1-4}$haloalkyl, halogen or nitro substituents; and R$_4$ represents a halogen atom.

3. The compound according to claim 2 wherein R$_1$ and R$_2$ are taken together with the interjacent nitrogen atom to represent a piperidyl, ring optionally substituted with one C$_{1-4}$alkyl group; R$_3$ represents a 2,6-dihalophenyl group; and R$_4$ represents a halogen atom.

4. A compound according to claim 3

5-bromo-6-(2-chloro-6-fluorophenyl)-7-(4-methylpiperidin-1-yl)-[1,2,4]triazolo[1,5-a]pyrimidine;

5-chloro-6-(2,6-dichlorophenyl)-7-(2-methylpiperidin-1-yl)-[1,2,4]triazolo[1,5-a]pyrimidine;

5-chloro-6-(2-chloro-6-fluorophenyl)-7-(3,6-dihydro-2H-pyridin-1-yl)-[1,2,4]triazolo[1,5-a]pyrimidine;

5-chloro-6-(2-chloro-6-fluorophenyl)-7-(2-ethylpiperidin-1-yl)-[1,2,4]triazolo[1,5-a]pyrimidine;

5-chloro-6-(2-chloro-6-fluorophenyl)-7-(2-methylpiperidin-1-yl)-[1,2,4]triazolo[1,5-a]pyrimidine;

5-chloro-6-(2-chloro-6-fluorophenyl)-7-(4-methylpiperidin-1-yl)-[1,2,4]triazolo[1,5-a]pyrimidine.

5. A method of combating fungus at a locus which comprises treating the locus with a fungicidally effective amount of a compound of formula I as defined in claim 1.

6. The method according to claim 5 wherein the fungus is a member of the oomycota.

7. A method of protecting a plant, seed or tuber from disease caused by a phytopathogenic fungus which comprises applying a fungicidally effective amount of a compound of formula I as defined in claim 1 to the plant stem or foliage, seed or tuber or to the soil or water in which the plant, seed or tuber is growing or is to be grown.

8. The method according to claim 7 wherein the disease is mildew, scab, blight or rot.

9. The method according to claim 7 wherein the formula I compound is applied at a rate of about 0.01 to 10 kg/ha.

10. A method of combating phytopathogenic fungus at a locus which comprises treating the locus with a fungicidally effective amount of a compound of formula I as defined in claim 2.

11. A fungicidal composition which comprises a carrier and a fungicidally effective amount of a compound of formula I as defined in claim 1.

12. The composition according to claim 11 having the formula I compound wherein R$_1$ represents a methyl, ethyl, propyl, heptyl, dodecyl, benzyl, dichlorocyclopropylmethyl, furylmethyl, trifluoromethylphenethyl, dimethoxyphenethyl, pentenyl, propynyl, dimethyloctadienyl, cyclopropyl, cyclopentyl, hydroxycyclopentyl, trimethylcyclopentyl, cyclohexyl, trimethylcyclohexyl, cyclooctyl, indanyl, or bicycloheptyl group; R$_2$ represents a hydrogen atom, methyl or ethyl group; or R$_1$ and R$_2$ together with the interjacent nitrogen atom represent a pyrrolidinyl, piperdiyl, or dihydropyridyl ring optionally substituted with one or more, C$_{1-4}$alkyl groups groups; R$_3$ represents a phenyl, fluorophenyl, chlorophenyl, chloronitrophenyl bromophenyl, chlorofluorophenyl, methylphenyl, propylphenyl, tert-butylphenyl, trifluoro-methylphenyl, methoxyphenyl, ethoxyphenyl, dimethoxy-phenyl, dichlorophenyl difluorophenyl, trimethoxyphenyl, trifluoromethoxyphenyl, biphenylyl, phenoxyphenyl, benzyloxyphenyl or naphthyl group; and R$_4$ represents a fluorine, chlorine, bromine or iodine atom or an amino, methylamino, dimethylamino, hydrazino, cyclopentylamino or bicyclo-heptylamino group.

13. The composition according to claim 12 wherein R$_1$ and R$_2$ are taken together with the interjacent nitrogen atom to represent pyrrolidinyl, piperidyl, or dihydropyridyl, ring optionally substituted with one or more $C_{1-4}$alkyl group; $R_3$ represents a phenyl group optionally substituted with one to three $C_{1-4}$alkyl, $C_{1-4}$haloalkyl, halogen or nitro substituents; and $R_4$ represents a or halogen atom.

* * * * *